US007749953B2

(12) United States Patent
Bab et al.

(10) Patent No.: US 7,749,953 B2
(45) Date of Patent: Jul. 6, 2010

(54) METHODS COMPOSITIONS AND ARTICLES OF MANUFACTURE FOR MODULATING BONE GROWTH

(75) Inventors: Itai Bab, Karmei Yossef (IL); Raphael Mechoulam, Jerusalem (IL); Andreas Zimmer, Bonn (DE); Esther Shohami, Mevasseret Zion (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 189 days.

(21) Appl. No.: 11/003,939

(22) Filed: Dec. 6, 2004

(65) Prior Publication Data

US 2005/0137159 A1 Jun. 23, 2005

Related U.S. Application Data

(63) Continuation-in-part of application No. PCT/IL03/00480, filed on Jun. 8, 2003.

(60) Provisional application No. 60/410,276, filed on Sep. 13, 2002, provisional application No. 60/385,881, filed on Jun. 6, 2002.

(51) Int. Cl.
*A61K 31/00* (2006.01)
*A61K 31/33* (2006.01)

(52) U.S. Cl. .......................... 514/1; 514/183

(58) Field of Classification Search ........................ None
See application file for complete search history.

(56) References Cited

U.S. PATENT DOCUMENTS

| | | | |
|---|---|---|---|
| 5,225,925 A | 7/1993 | Grubb et al. | |
| 6,100,259 A | 8/2000 | Xiang et al. | |
| 6,166,066 A | 12/2000 | Makriyannis et al. | |
| 6,352,972 B1 | 3/2002 | Nimni et al. | |
| 6,352,973 B1 | 3/2002 | Tam | |
| 6,391,909 B1 | 5/2002 | Makriyannis et al. | |
| 6,413,998 B1 | 7/2002 | Petrie et al. | |
| 6,440,421 B1 | 8/2002 | Cornish et al. | |
| 6,448,288 B1 | 9/2002 | Burstein et al. | |
| 6,462,019 B1 | 10/2002 | Mundy et al. | |
| 6,525,087 B2 | 2/2003 | Mittendorf et al. | |
| 6,531,636 B1 | 3/2003 | Mechoulam et al. | |
| 2002/0077322 A1 | 6/2002 | Ayoub | |
| 2002/0111377 A1 | 8/2002 | Stinchcomb | |
| 2002/0119972 A1 | 8/2002 | Leftheris et al. | |
| 2004/0127572 A1* | 7/2004 | Carley et al. | 514/625 |

FOREIGN PATENT DOCUMENTS

| | | |
|---|---|---|
| EP | 0444451 | 7/1991 |
| EP | 0504038 | 3/1992 |
| EP | 0570920 | 5/1993 |
| EP | 0451867 | 3/1996 |
| EP | 0499242 | 6/1996 |
| WO | WO 92/14481 | 9/1992 |
| WO | WO 94/12466 | 9/1994 |
| WO | WO 98/32441 | 7/1998 |
| WO | WO 98/41519 | 9/1998 |
| WO | WO 99/26612 | 3/1999 |
| WO | WO 99/51560 | 10/1999 |
| WO | WO 01/09773 | 8/2001 |
| WO | WO 01/97793 | 12/2001 |
| WO | WO 02/42269 | 5/2002 |
| WO | WO 2004/078261 | 9/2004 |

OTHER PUBLICATIONS

Opalinska et al. Nature Reviews Drug Discovery, 2002, vol. 1, P. 503-514.*
Armstrong et al Neuroscience 2001, vol. 106, pp. 201-216.*
Platt, Nature 1998, vol. 392 supplement, pp. 11-17.*
Gage, Nature 1998, vol. 392 supplement, pp. 18-24.*
Bocchetta et al. Oncogene 2004, vol. 23, pp. 6484-6491.*
Taniegra et al: American Family Physician 2004, vol. 69, pp. 333-339.*
Hanus et al. PNAS 1999, vol. 96, pp. 14228-14233.*
Heymann et al. Drug Discovery Today 2005, vol. 10, pp. 242-247.*
Houry et al. "Benzoxocin and Benzoxonin Derivatives. Novel Groups of Terpenophenols With Central Nervous System Activity", Journal of Medicinal Chemistry, 17(3): 287-293, 1974.
Houry et al. "Benzoxocin and Benzoxonin Derivatives. Novel Groups of Terpenophenols With Central Nervous System Activity. A Correction", Journal of Medicinal Chemistry, 18(9): 951-952, 1975.
Howlett et al. "International Union of Pharmacology. XXVII. Classification of Cannabinoid Receptors", Pharmacological Reviews, 54(2): 161-202, 2002.
Hutvágner et al. "RNAi: Nature Abhors A Double-Strand", Current Opinion in Genetics & Development, 12: 225-232, 2002.
Ishac et al. "Inhibition of Exocytotic Noradrenaline Release by Presynaptic Cannabinoid CB1 Receptors on Peripheral Sympathetic Nerves", British Journal of Pharmacology, 118: 2023-2028, 1996.
Itoh et al. "Inhibition of Urokinase Receptor (uPAR) Expression by RNA-Cleaving Catalytic DNA (DNAzyme) Containing Antisense uPAR", Molecular Therapy, 5(5): S134, 2002. Abstract 409.
Parfitt et al. "Bone Histomorphometry: Standardization of Nomenclature, Symbols, and Units", Journal of Bone and Mineral Research, 2(6): 595-610, 1987.
Katona et al. "Presynaptically Located CB1 Cannabinoid Receptors Regulate GABA Release From Axon Terminals of Specific Hippocampal Interneurons", The Journal of Neuroscience, 19(11): 4544-4558, 1999.
Járai et al. "Cannabinoid-Induced Mesenteric Vasodilation Through An Endothelial Site Distinct From CB1 of CB2 Receptors", Proc. Natl. Acad. Sci. USA, 96(24): 14136-14141, 1999.
Kato et al. "Establishment of An Osteoid Preosteocyte-Like Cell MLO-A5 That Spontaneously Mineralizes in Culture", Journal of Bone and Mineral Research, 16(9):1622-1633, 2001.

(Continued)

*Primary Examiner*—Tracy Vivlemore
(74) *Attorney, Agent, or Firm*—Browdy and Neimark, PLLC

(57) ABSTRACT

Novel methods and pharmaceutical compositions suitable for modulating bone growth and remodeling, preventing bone diseases, inducing bone growth or repair by cannabinoid receptor-mediated effects on bone cells is disclosed. Methods of identifying bone growth modulating agents are also disclosed.

9 Claims, 14 Drawing Sheets
(7 of 14 Drawing Sheet(s) Filed in Color)

OTHER PUBLICATIONS

Klein et al. "The Cannabinoid System and Immune Modulation", Journal of Leukocyte Biology, 74: 486-496, 2003.

Klein et al. "Cannabinoid Receptors and Immunity", Immunology Today, 19(8): 373-381, 1998.

Kronenwett et al. "Oligodeoxyribonucleotide Uptake in Primary Human Hematopoietic Cells Is Enhanced by Cationic Lipids and Depends on the Hematopoietic Cell Subset", Blood, 91(3): 852-862, 1998.

Lavigne et al. "Enhanced Antisense Inhibition of Human Immunodeficiency Virus Type 1 in Cell Cultures by DLS Delivery System", Biochemical and Biophysical Research Communications, 237: 566-571, 1997.

Ledent et al. "Unresponsiveness to Cannabinoids and Reduced Addictive Effects of Opiates in CB1 Receptor Knockout Mice", Science, 283(5400): 401-404, 1999.

Lee et al. "Differential Expression of Cannabinoid CB2 Receptor mRNA in Mouse Immune Cell Subpopulations and Following B Cell Stimulation", European Journal of Pharmacology, 423:235-241, 2001.

Lonberg et al. "Human Antibodies From Transgenic Mice", International Rviews in Imunology, 13: 65-93, 1995.

Lonberg et al. "Antigen-Specific Human Antibodies From Mice Comprising Four Distinct Genetic Modifications", Nature, 368:856-859, 1994.

Luft "Making Sense Out of Antisense Oligodeoxynucleotide Delivery: Getting There Is Half the Fun", Journal of Molecular Medicine, 76: 75-76, 1998.

Marks et al. "By-Passing Immunization: Building High Affinity Human Antibodies by Chain Shuffling", Bio/Technology, 10: 779-783, 1992.

Marks et al. "By-Passing Immunization. Human Antibodies From V-Gene Libraries Displayed on Phage", Journal of Molecular Biology, 222: 581-597, 1991.

Matsuda et al. "Structure of A Cannabinoid Receptor and Functional Expression of the Cloned cDNA", Nature, 346: 561-564, 1990.

Matveeva et al. "Prediction of Antisense Oligonucleotide Efficacy by In Vitro Methods", Nature Biotechnology, 16: 1374-1375, 1998.

Mechoulam et al. "Recent Advances in the Chemistry and Biochemistry of Cannabis", Chemical Reviews, 76(1): 75-112, 1976.

Mechoulam et al. "Towards Cannabinoid Drugs—Revisited", Progress in Medicinal Chemistry, 35(Chap.5): 199-243, 1998.

Mechoulam et al. "Endocannabinoids", European Journal of Pharmacology, 359: 1-18, 1998.

Mechoulam et al. "Synthesis and Biological Activity of Five Tetrahydrocannabinol Metabolites", Journal of the american Chemical Society, 94(22): 7930-7931, 1972.

Mechoulam et al. "Stereochemical Requirements for Cannabinoid Activity", Journal of Medicinal Chemistry, 23(10): 1068-1072, 1980.

Mechoulam et al. "Chemical Basis of Hashish Activity", Science, 169(3945): 611-612, 1970.

Mechoulam et al. "Synthesis of the Individual, Pharmacologically Distinct, Enantiomers of A Tetrahydrocannabinol Derivative", Tetrahedron: Asymmetry, 1(5): 315-318, 1990.

Larrick et al. "PCR Amplification of Antibody Genes", Methods: A Companion to Methods in Enzymology, 2(2): 106-110, 1991.

Morrison "Success in Specification", Nature, 368: 812-813, 1994.

Muller et al. "Single-Step Induction of Mammary Adenocarcinoma in Transgenic Mice Bearing the Activated C-Neu Oncogene", Cell, 54: 105-115, 1988.

Munro et al. "Molecular Characterization of A Peripheral Receptor for Cannabinoids", Nature, 365: 61-65, 1993.

Neuberger "Generating High-Avidity Human Mabs in Mice", Nature Biotechnology, 14: 826-827, 1996.

Noe et al. "Cannabinoid Receptor Agonists Enhance Syncytia Formation in MT-2 Cells Infected With Cell Free HIV-1MN", Drugs of Abuse, Immunomodulation, and AIDS, Plenum Press, p. 223-229, 1998.

Noe et al. "Modulation of CB1 mRNA Upon Activation of Murine Splenocytes", Neuroimmune Circuits, Drugs of Abuse, and Infectious Diseases, p. 215-221, 2001.

Ohkubo et al. "Ecto-Alkaline Phosphatase in NG108-15 Cells: A Key Enzyme Mediating P1 Antagonist-Sensitive ATP Response", British Journal of Pharmacology, 131(8): 1667-1672, 2000.

Pack et al. "Improved Bivalent Miniantibodies, With Identical Avidity as Whole Antibodies, Produced by High Cell Density Fermentation of *Escherichia coli*", Bio/Technology, 11: 1271-1277, 1993.

Panikashvili et al. "An Endogenous Cannabinoid (2-AG) Is Neuroprotective After Brain Injury", Nature, 413: 527-531, 2001.

Parolaro "Presence and Functional Regulation of Cannabinoid Receptors in Immune Cells", Life Sciences, 65(6/7): 637-644, 1999.

Pertwee "Pharmacology of Cannabinoid Receptor Ligands", Current Medicinal Chemistry, 6(8): 635-664, 1999.

Shire et al. "Molecular Cloning, Expression and Function of the Murine CB2 Peripheral Cannabinoid Receptor", Biochimica et Biophysica Acta, 1307: 132-136, 1996.

Piomelli et al. "The Endocannabinoid System as a Target for Therapeutic Drugs", Trends in Pharmacological Sciences (TiPS), 21: 218-224, 2000.

Presta "Antibody Engineering", Current Opinion in Structural Biology, 2: 593-596, 1992.

Inbar et al. "Localization of Antibody-Combining Sites Within the Variable Portions of Heavy and Light Chains", Proc. Natl. Acad. Sci. USA, 69(9): 2659-2662, 1972.

Rajur et al. "Covalent Protein-Oligoneucleotide Conjugates for Efficient Delivery of Antisense Molecules", Bioconjugate Chemistry, 8(6): 935-940, 1997.

Rhee et al. "Cannabinol Derivatives: Binding to Cannabinoid Receptors and Inhibition of Adenylylcyclase", Journal of Medicinal Chemistry, 40(20): 3228-3233, 1997.

Riechmann et al. "Reshaping Human Antibodies for Therapy", Nature, 332: 323-327, 1988.

Santoro et al. "A General Purpose RNA-Cleaving DNA Enzyme", Proc. Natl. Acad. Sci. USA, 94: 4262-4266, 1997.

Sharp "RNA Interference—2001", Genes & Development, 15: 485-490, 2001.

Uno et al. Antisense-Mediated Suppression of Human Heparanase Gene Expression Inhibits Pleural Dissemination of Human Cancer Cells, Cancer Research, 61: 7855-7860, 2001.

Tsou et al. "Immunohistochemical Distribution of Cannabinoid CB1 Receptors in the Rat Central Nervous System", Neuroscience, 83(2): 393-411, 1998.

Verhoeyen et al. "Reshaping Human Antibodies: Grafting an Antilysozyme Activity", Science, 239(4847): 1534-1536, 1988.

Vollmer et al. "Role of the Central Autonomic Nervous System in the Hypotension and Bradycardia Induced by (-)-Δ9-Trans-Tetrahydrocannabinol", Journal of Pharmacology and Pharmacy, 26:186-192, 1973.

Wagner et al. "Cardiovascular Actions of Cannabinoids and Their Generation During Shock", Journal of Molecular Medicine, 76: 824-836, 1998.

Waksman et al. "The Central Cannabinoid Receptor (CB1) Mediates Inhibition of Nitric Oxide Production by Rat Microglial Cells", The Journal of Pharmacology and Experimental Therapeutics, 288(3): 1357-1366, 1999.

Walton et al. "Prediction of Antisense Oligonucleotide Binding Affinity to A Structured RNA Target", Biotechnology and Bioengineering, 65(1): 1-9, 1999.

Welch et al. "Ribozyme Gene Therapy for Hepatitis C Virus Infection", Clinical and Diagnostic Virology, 10: 163-171, 1998.

Welch et al. "Expression of Ribozymes in Gene Transfer Systems to Modulate Target RNA Levels", Current Opinion in Biotechnology, 9: 486-496, 1998.

Whitlow et al. "Single-Chain Fv Proteins and Their Fusion Proteins", Methods: A Companion to Methods in Enzymology, 2(2): 97-105, 1991.

Zimmer et al. "Increased Mortality, Hypoactivity, and Hypoalgesia in Cannabinoid CB1 Receptor Knockout Mice", Proc. Natl. Acad. Sci. USA, 96: 5780-5785, 1999.

Zou et al. "CpG Oligonucleotides: Novel Regulators of Osteoclast Differentiation", The FASEB Journal, 16: 274-282, 2002.

Travis "Boning Up. Turning On Cells That Build Bone and Turning Off Ones That Destroy Them", Science News, 157(3): 7 P., 2000.

Goya et al. "Recent Advances in Cannabinoid Receptor Agonists and Antagonists", Expert Opinion on Therapeutic Patents, 10(10): 1529-1538, 2000.

Barth "Cannabinoid Receptor Agonists and Antagonists", Expert Opinion on Therapeutic Patents, 8(3): 301-313, 1998.

Alexander et al. "Human Parathyroid Hormone 1-34 Reverses Bone Loss in Ovariectomized Mice", Journal of Bone and Mineral Research, 16(9): 1665-1673, 2001.

Aoki et al. "In Vivo Transfer Efficiency of Antisense Oligonucleotides Into the Myocardium Using HVJ-Liposome Method", Biochemical and Biophysical Research Communications, 231: 540-545, 1997.

Axelrod et al. "Cannabinoid Receptors and Their Endogenous Agonist, Anandamide", Neurochemical Research, 23(5): 575-581, 1998.

Bernstein et al. "Role for A Bidentate Ribonuclease in the Initiation Step of RNA Interference", Nature, 409: 363-366, 2001.

Porter et al. "The Hydrolysis of Rabbit γ-Globulin and Antibodies With Crystalline Papain", Biochemical Journal, 73: 119-126, 1959.

Bird et al. "Single-Chain Antigen-Binding Proteins", Science, 242(4877): 423-426, 1988.

Boerner et al. "Production of Antigen-Specific Human Monoclonal Antibodies From In Vitro-Primed Human Splenocytes", The Journal of Immunology, 147(1): 86-95, 1991.

Brantl "Antisense-RNA Regulation and RNA Interference", Biochimica et Biophysica Acta, 1575: 15-25, 2002.

Breaker et al. "A DNA Enzyme With Mg2+-Dependent RNA Phosphoesterase Activity", Chemistry & Biology, 2: 655-660, 1995.

Breivogel et al. "Evidence for A New G Protein-Coupled Cannabinoid Receptor in Mouse Brain", Molecular Pharmacology, 60(1): 155-163, 2001.

Burgener et al. "Fluoride Increases Tyrosine Kinase Activity in Osteoblast-Like Cells: Regulatory Role for the Stimulation of Cell Proliferation and Pi Transport Across the Plasma Membrane", Journal of Bone and Mineral Research, 10(1): 164-171, 1995.

Burstein et al. "Synthetic Nonpsychotropic Cannabinoids With Potent Antiinflammatory, Analgesic, and Leukocyte Antiadhesion Activities", Journal of Medicinal Chemistry, 35(17): 3135-3141, 1992.

Calignano et al. "Antinoceptive Acitvity of the Endogenous Fatty Acid Amide, Palmitylethanolamide", European Journal of Pharmacology, 419: 191-198, 2001.

Caplan "Mesenchymal Stem Cells", Journal of Orthopaedic Research, 9: 641-650, 1991.

Carayon et al. "Modulation and Functional Involvement of CB2 Peripheral Cannabinoid Receptors During B-Cell Differentiation", Blood, 92(10): 3605-3615, 1998.

Chakrabarti et al. "Cloning and Sequencing of A cDNA Encoding the Mouse Brain-Type Cannabinoid Receptor Protein", DNA Sequence—The Journal of Sequencing and Mapping, 5: 385-388, 1995.

Cole et al. "The EBV-Hybridoma Technique and Its Application to Human Lung Cancer", Monoclonal Antibodies and Cancer Therapy, p. 77-96, 1985.

Cravatt et al. "Supersensitivity to Anandamide and Enhanced Endogenous Cannabinoid Signaling in Mice Lacking Fatty Acid Amide Hydrolase", Proc. Natl. Acad. Sci. USA, 98(16): 9371-9376, 2001.

Cullen "RNA Interference: Antiviral Defense and Genetic Tool", Nature Immunology, 3(7): 597-599, 2002.

Khachigian "DNAzymes: Cutting A Path to A New Class of Therapeutics", Current Opinion in Molecular Therapeutics, 4(2): 119-121, 2002.

Devane et al. "A Novel Probe for the Cannabinoid Receptor", Journal of Medicinal Chemistry, 35(11): 2065-2069, 1992.

Devane et al. "Determination and Characterization of A Cannabinoid Receptor in Rat Brain", Molecular Pharmacology, 34: 605-613, 1988.

Devane et al. "Isolation and Structure of A Brain Constituent That Binds to the Cannabinoid Receptor", Science, 258(5090): 1946-1949, 1992.

Di Marzo et al. "Levels, Metabolism, and Pharmacological Activity of Anandamide In CB1, Non-CB2 Receptor-Mediated Actions of Anandamide in Mouse Brain", Journal of Neurochemistry, 75: 2434-2444, 2000.

Edery et al. "Structural Requirements for Cannabinoid Activity", Annals New York Academy of Sciences, 191:40-53, 1971.

Egertová et al. "Localisation of Cannabinoid Receptors in the Rat Brain Using Antibodies to the Intracellular C-Terminal Tail of CB1", The Journal of Comparative Neurology, 422: 159-171, 2000.

Felder et al. "Anandamide, An Endogenous Cannabimimetic Eicosanoid, Binds to the Cloned Human Cannabinoid Receptor and Stimulates Receptor-Mediated Signal Transduction", Proc. Natl. Acad. Sci. USA, 90: 7656-7660, 1993.

Fingl et al. "General Principles", The Pharmacological Basis of Therapeutics, 5th Ed., Sec.I(Chap.I): 1, 1975.

Fishwild et al. "High-Avidity Human IgGK Monoclonal Antibodies From A Novel Strain of Minilocus Transgenic Mice", Nature Biotechnology, 14: 845-851, 1996.

Galiègue et al. "Expression of Central and Peripheral Cannabinoid Receptors in Human Immune Tissues and Leukocyte Subpopulations", European Journal of Biochemistry, 232: 54-61, 1995.

Gaoni et al. "The isolation and Structure of $\Delta^1$-Tetrahydrocannabinol and Other Neutral Cannabinoids From Hashish", Journal of the American Chemical Society, 93(l):217-224, 1971.

Gérard et al. "Nucleotide Sequence of A Human Cannabinoid Receptor cDNA", Nucleic Acids Research, 18(23): 7142, 1990.

Gewirtz "Oligonucleotide Therapeutics: Clothing the Emperor", Current Opinion in Molecular Therapeutics, 1(3): 2970306, 1999.

Griffin et al. "Cloning and Pharmacological Characterization of the Rat CB2 Cannabinoid Receptor", The Journal of Pharmacology and Experimental Therapeutics, 292(3): 886-894, 2000.

Hammond et al. "Post-Transcriptional Gene Silencing by Double-Stranded RNA", Nature Reviews, 2: 110-119,2001.

Hanuš et al. "Two New Unsaturated Fatty Acid Ethanolamides in Brain That Bind to the Cannabinoid Receptor", Journal of Medicinal Chemistry, 36(20): 3032-3034, 1993.

Hanuš et al. "2-Arachindonyl Glyceryl Ether, An Endogenous Agonist of the Cannabinoid CB1 Receptor", Proc. Natl. Acad. Sci. USA, 98(7): 3662-3665, 2001.

Holmlund et al. "Toward Antisense Oligonucleotide Therapy for Cancer: ISIS Compounds in Clinical Development", Current Opinion in Molecular Therapeutics, 1(3): 372-385, 1999.

Hoogenboom et al. "By-Passing Immunisation. Human Antibodies From Synthetic Repertoires of Germline VH Gene Segments Rearranged In Vitro", Journal of Molecular Biology, 227: 381-388, 1992.

Wikepedia: Ankylosing Spondylitis, http://en.wikipedia.org/wiki/Ankylosing_spondylitis (Aug. 10, 2009).

Wikepedia: Osteoarthritis, http://en.wikipedia.org/wiki/Osteoarthritis (Aug. 10, 2009).

Wikepedia: Osteoporosis, http://en.wikipedia.org/wiki/Osteoporosis (Aug. 10, 2009).

Wikepedia: Gout, http://en.wikipedia.org/wiki/Gout (Aug. 10, 2009).

* cited by examiner

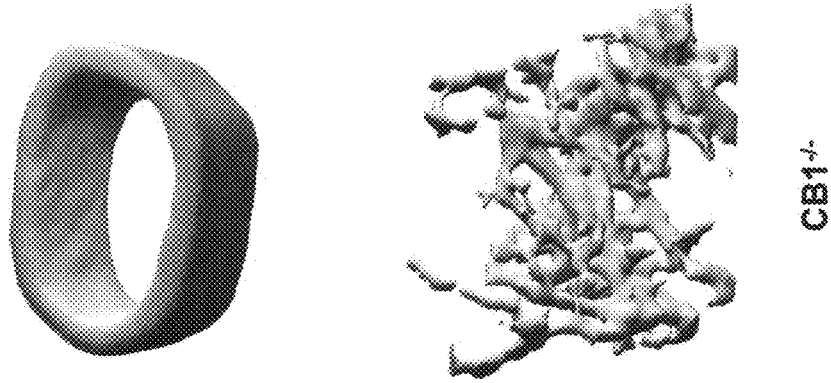
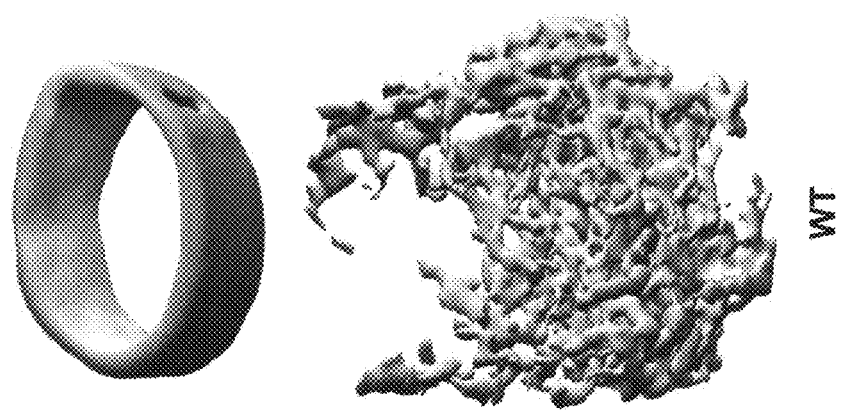

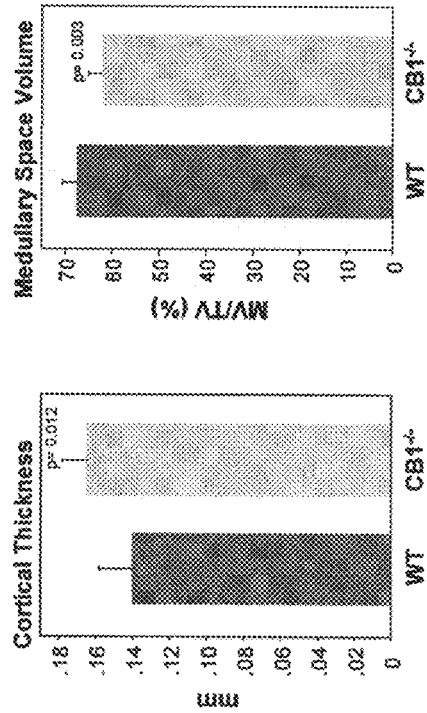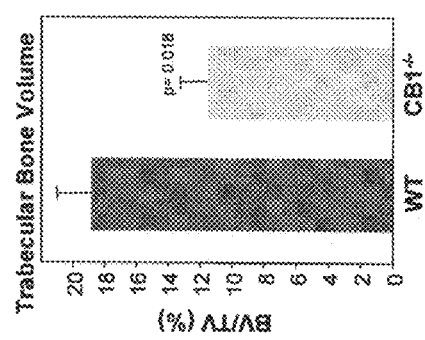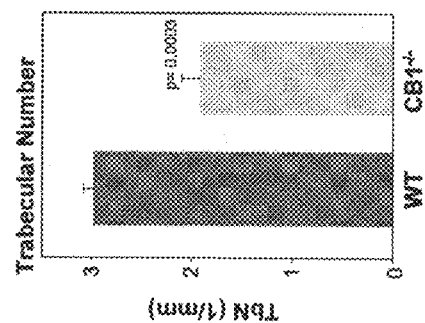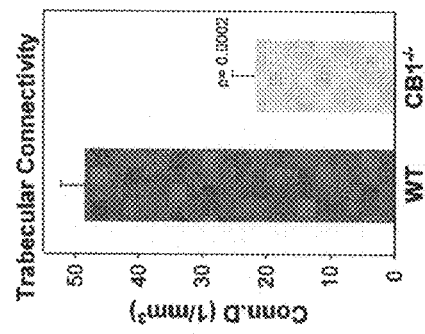

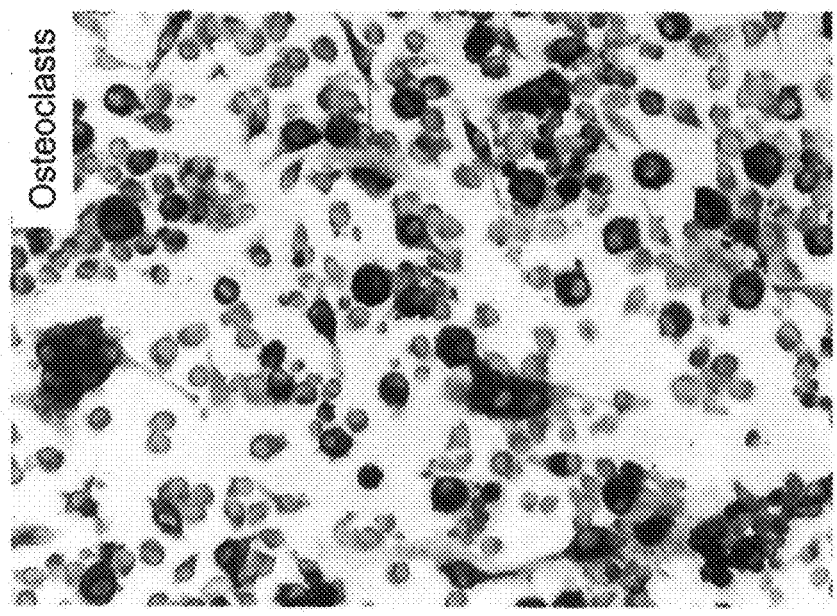
FIG. 6B Osteoclasts
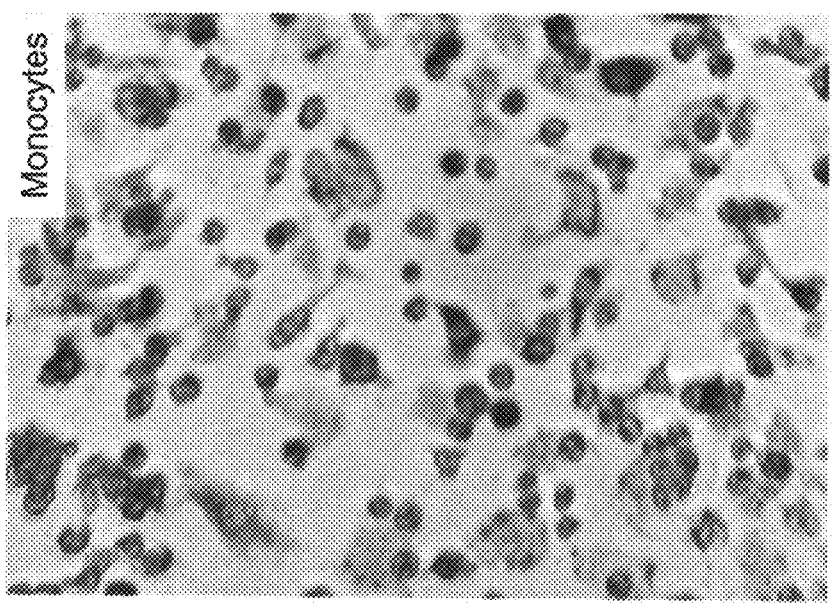
FIG. 6A Monocytes
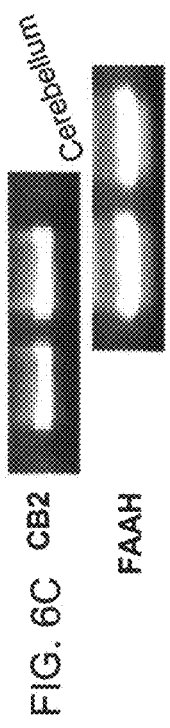
FIG. 6C  CB2   FAAH   Cerebellum

METHODS COMPOSITIONS AND ARTICLES OF MANUFACTURE FOR MODULATING BONE GROWTH

This is a continuation-in-part of PCT/IL03/00480, filed Jun. 8, 2003, which claims the benefit of priority of U.S. provisional patent application No. 60/410,276, filed Sep. 13, 2002 and of U.S. provisional patent application No. 60/385,881, filed Jun. 6, 2002. Priority is claimed of all of the above-identified applications.

FIELD AND BACKGROUND OF THE INVENTION

The present invention relates to methods of modulating bone growth and, remodeling, methods of treating or preventing bone diseases, methods of inducing and stimulating bone growth and peak bone mass or repair, pharmaceutical compositions for modulating bone growth, articles of manufacturing and methods of identifying bone growth modulating agents. Specifically, the present invention employs regulating the expression or activity of cannabinoid receptors in bone cells which in turn modulates bone growth and remodeling.

Naturally occurring cannabinoids may be divided into two categories, plant-derived and endogenous. Plant-derived cannabinoids are known to elicit dramatic psychobehavioral effects, exemplified by the well-known $\Delta^9$-tetrahydrocannabinol (THC), the psychotropic principle in marijuana. They are also known to have complex cardiovascular effects, a prominent component of which is hypotension [Vollmer et al., J. Pharm. Pharmacol. 26:186-198 (1974)]. Endogenous cannabinoids (endocannabinoids) are a class of lipid-like molecules that share receptor binding sites with plant-derived cannabinoids and mimic many of their neurobehavioral effects [Mechoulam et al., Adv. Exp. Bio. Med. 402:95-101 (1996)]. Two endocannabinoids have been characterized in some detail: arachidonyl ethanolamide (anandamide) [Devane et al., Science 258:1946-1949 (1992); Felder et al., Proc. Natl. Acad. Sci. USA. 90:7656-7660 (1993)] and 2-arachidonoyl glycerol (2-AG) [Mechoulam et al., Biochem. Pharmacol 50:83-90 (1995)].

Additional natural or synthetic cannabinoids are described in U.S. Pat. Nos. 4,371,720, 5,013,387, 5,081,122, 5,292,736, 5,461,034, 5,618,955, 6,166,066 and 6,531,636; International Patent applications WO 01/9773, WO 97/29079, WO 99/02499, WO 98/41519, and WO 94/12466; European Patent Nos. EP 0570920 and EP 0444451; French Patent No. FR 2735774; and Israeli Pat. Nos. IL 01/00551 and IL 99/00187; Gaoni and Mechoulam, J. Amer. Chem. Soc. 93, 217 (1971); Mechoulam et al., Science 169, 611 (1970); Edery et al., Ann. N.Y. Acad. Sci., 191, 40 (1971); Mechoulam et al., J. Amer. Chem. Soc., 94, 7930 (1972); R. Mechoulam (ed.), "Marijuana: Chemistry, Metabolism, Pharmacology, and Clinical Effects" Academic Press, 1973, New-York; Houry et al., J. Med. Chem., 17, 287 (1974); Houry et al., J. Med. Chem., 18, 951 (1975); Mechoulam et al., Chem. Reviews, 76, 75 (1976); Mechoulam et al., J. Med. Chem., 23, 1068 (1980); Srebnik et al., J. Chem. Soc., Perkin Trans. I, 2881 (1984); Mechoulam et al., Tetrahedron: Asymmetry, 1, 315 (1990); Devane et al., Science, 258, 1946 (1992); Burstein et al., J. Med. Chem., 35, 3135 (1992); Hanus et al., J. Med. Chem., 36, 3032 (1993); Mechoulam et al., Biochem. Pharmacol., 50, 83 (1995); Sheskin et al., J. Med. Chem., 40, 659 (1997); Rhee et al., J. Med. Chem. 40, 3228 (1997); and Hanus et al., PNAS, 98, 3662 (2001).

Endocannabinoids exert their effects by binding to specific receptors thereby activating neurotransmitters and hormone regulators [Piomelli et al., Trends Pharmacol. Sci. 21: 218-224 (2000); Petwee, R. G., Curr. Med. Chem. 6:635-664 (1999); and Devane et al., J. Med. Chem. 35: 2065-2069)].

To date, two types of high-affinity cannabinoid receptors have been identified by molecular cloning: (i) CB1 receptors, present mostly in brain [Devane et al., Mol. Pharmacol. 34:605-613 (1988); Matsuda et al., Nature 346:561-564 (1990)] but also in some peripheral tissues [Shire et al., J. Biol. Chem. 270:3726-3731 (1995); Ishac et al., Br. J. Pharmacol. 118:2023-2028 (1996)], and (ii) CB2 receptors, present on macrophages in the spleen [Munro et al., Nature 365:61-65 (1993)]. Other types or subtypes of cannabinoid receptors have been recently described, designated CB1-like receptors, CB2-like receptors, and non-CB1 non-CB2 receptors [Hanus et al., J. Pharmacol. Exper. Therapeutics 54: 161-202 (2002)].

The physiological roles of endogenous cannabinoids and the pathways of endocannabinoid signaling are the subject of intense investigation and have been reported to affect processes in the nervous, cardiovascular, immune, and reproductive systems [Mechoulam et al., Eur. J. Pharmacol. 359: 1-18 (1998); Axelrod and Felder, Neurochem. Res. 23: 575-581 (1998); Wagner et al., J. Mol. Med. 76: 824-836 (1999); and Klein et al., Immunol. Today 19: 373-381 (1998)].

Accordingly, cannabinoids or cannabinoids receptor ligands have been used or described as useful therapeutic agents for treating a variety of medical disorders.

Thus, THC has been extensively used to prevent excessive weight loss by cancer or AIDS patients [Mechoulam et al., E. Prog. Med. Chem. 35: 199-243 (1998)].

U.S. Pat. No. 5,939,429 discloses use of agonists of CB1 receptors as well as other cannabinoid receptors to treat cardiovascular conditions, including hemorrhagic shock and in other conditions associated with excessive vasoconstriction, such as hypertension, peripheral vascular disease, cirrhosis of the liver, and certain forms of angina pectoris. In addition it teaches use of antagonists of CB1 and other cannabinoid receptors for treating hypotension which is caused by endotoxin activation of macrophages.

U.S. Pat. No. 6,166,066 discloses use of cannabinoids which are selective for the CB2 receptor as immunosuppressive agents for preventing tissue rejection in organ transplant patients and for treating autoimmune associated diseases.

U.S. application Ser. No. 09/779,109 discloses use of cannabinoids receptor modulators for treating respiratory or non-respiratory leukocyte-activation associated diseases. Exemplary non-respiratory cannabinoid receptor-mediated diseases include transplant rejection, rheumatoid arthritis, multiple sclerosis, inflammatory bowel disease, lupus, graft v. host disease, T-cell mediated hypersensitivity disease, psoriasis, Hashimoto's thyroiditis, Guillain-Barre syndrome, cancer, contact dermatitis, allergic rhinitis, and ischemic or reperfusion injury.

U.S. application Ser. No. 10/032,163 discloses a method of increasing the activity of a cannabinoid agonist that binds specifically to an endogenous cannabinoid receptor, so as to protect the cells against glutamate-induced neurotoxicity.

Yet, while cannabinoids or cannabinoid receptor ligands have been suggested for use as therapeutic agents, application of cannabinoids for treating or preventing bone-related diseases has never been described nor suggested in prior art.

While reducing the present invention to practice, the inventors of the present invention surprisingly uncovered the major role of endocannabinoids in modulating bone growth and remodeling, thus indicating the potential benefits of using cannabinoids or cannabinoids receptor ligands as therapeutic agents for treating bone diseases and injuries as well as promoting bone formation or inhibiting bone resorption.

Bone is subject to constant breakdown and resynthesis in a complex process mediated by osteoblasts, which produce new bone, and osteoclasts, which destroy bone. This process is referred to as bone remodeling. The activities of these cells are regulated by a large number of cytokines, hormones and growth factors, many of which have now been identified and cloned.

There is a plethora of conditions which are characterized by the need to promote bone formation and/or to inhibit bone resorption. Perhaps the most obvious is the case of bone fractures, where it would be desirable to stimulate bone growth and to hasten and complete bone repair. Agents that enhance bone formation would also be useful in endosseous implants and facial reconstruction procedures, and of great importance in the growing field of prosthetic and therapeutic bone implants. Other bone deficit conditions include bone segmental defects, periodontal disease, metastatic bone disease, osteolytic bone disease and conditions where connective tissue repair would be beneficial, such as healing or regeneration of cartilage defects or injury. Also of great significance is the chronic condition of osteoporosis, including age-related osteoporosis and osteoporosis associated with post-menopausal hormone status. Other conditions characterized by the need for bone growth include primary and secondary hyperparathyroidism, disuse osteoporosis, diabetes-related osteoporosis, osteoporosis associated with depression and hypogonadism and glucocorticoid-related osteoporosis.

On the other hand, there are conditions which are characterized by the need to inhibit bone formation or to promote bone resorption. These include certain stages of Paget's disease, blastic metastatic bone cancer, Hodgkin's lymphoma, degenerative sclerosis and osteomyelitis. Agents known to be effective in inhibition of bone growth, and in bone resorption, are the cyclooxygenase inhibitors, 1, 25 $(OH)_2$ vitamin D3, the glucocorticoids, omeprazole, the serum protein fetuin, noggin, blockers of beta adrenergic receptors, chordin and DAN proteins and high concentrations of TGF-beta. However, all of the abovementioned agents (particularly the glucocorticoids and other hormones) are known to exert their influence on a wide variety of tissues, and as such are unsuited for pharmacological applications in bone diseases.

Various therapeutic agents and approaches to treatment of bone related diseases have been disclosed in patent publications.

U.S. Pat. No. 5,461,034 discloses osteogenic growth polypeptides identified from regenerating bone marrow, for the enhancement of bone formation and bone marrow in preparation for bone marrow transplant. U.S. Pat. No. 5,280, 040 discloses antiestrogenic, oral contraceptive compounds, 3,4-diarylchromans, described as useful in the treatment of osteoporosis. U.S. Pat. No. 6,352,973 discloses a recombinant protein containing a bone morphogenic polypeptide of the TGF-beta superfamily of cytokines originally isolated from blood serum, for enhancing bone growth. U.S. Pat. No. 6,462,019 discloses inhibitors of proteasomal activity and production for inhibiting osteoclastic activity and stimulating bone growth, based on the observation that mice lacking proteasomal activity develop the condition of excess bone formation known as osteopetrosis.

International patent application No. 92/15615 discloses a protein derived from a porcine pancreas which acts to depress serum calcium levels for treatment of bone disorders that cause elevation of serum calcium levels.

International patent application No. 92/14481 discloses a composition for inducing bone growth which contains activin and bone morphogenic protein.

European Patent Application No. 504 938 discloses the use of di- or tripeptides which inhibit cysteine protease in the treatment of bone diseases.

European Patent Application No. 499 242 discloses the use of cell growth factor compositions thought to be useful in bone diseases involving bone mass reduction because they cause osteoblast proliferation.

European Patent Application No. 451 867 discloses parathyroid hormone peptide antagonists for treating dysbolism associated with calcium or phosphoric acid, such as osteoporosis.

Yet, currently no satisfactory pharmaceutical approaches to managing bone defects are available. Bone fractures are still treated exclusively using casts, braces, anchoring devices and other strictly mechanical means. Further bone deterioration associated with osteoporoses has been treated with estrogens or bisphosphonates, which may have drawbacks for some individuals.

Although the Bone Morphogenic Proteins (BMPs) are potent stimulators of bone formation in vitro and in vivo, there are disadvantages to their use as therapeutic agents to enhance bone healing. Receptors for the bone morphogenetic proteins have been identified in many tissues, and the BMPs themselves are expressed in a large variety of tissues in specific temporal and spatial patterns. This suggests that BMPs may have effects on many tissues in addition to bone, potentially limiting their usefulness as therapeutic agents when administered systemically. Moreover, since they are peptides, they would have to be administered by injection. These disadvantages impose severe limitations to the development of BMPs as therapeutic agents.

The fluorides, suggested also for the purpose of enhancing bone formation, have a mode of action which may be related to tyrosine phosphorylation of growth factor receptors on osteoblasts, as described, for example, Burgener et al. J Bone Min Res (1995) 10:164-171, but administration of fluorides is associated with increased bone fragility, presumably due to adverse effects on bone mineralization.

Parathyroid hormone, currently considered the leading agent for metabolic enhancement of bone formation, is inherently problematic, since it is only administered by injection.

Thus, although various approaches have been tried, such as described above, there remains a need for additions to the repertoire of agents which can be used to treat these conditions.

There is thus a widely recognized need for, and it would be highly advantageous to have novel effective bone growth modulating agents acting through normal signaling pathways, which can be used to treat these conditions. Accordingly, the present invention provides novel methods, pharmaceutical compositions and articles of manufacture for modulating bone growth and for treating or preventing bone defects based on regulating cannabinoid receptors.

SUMMARY OF THE INVENTION

According to one aspect of the present invention there is provided a method of modulating bone growth and/or bone remodeling, comprising regulating an expression or activity of at least one cannabinoid receptor, thereby modulating bone growth and/or bone remodeling.

According to another aspect of the present invention there is provided a method of treating or preventing a bone disease in a subject in need thereof, comprising regulating an expression or activity of at least one cannabinoid receptor of the subject, thereby treating or preventing the bone disease in the subject.

According to yet another aspect of the present invention there is provided a method of inducing bone growth and/or repair in a subject in need thereof, comprising: (a) isolating bone cells; (b) regulating an expression or activity of at least one cannabinoid receptor of the bone cells; and (c) administering the bone cells resulting from step (b) to the subject, thereby inducing bone growth or repair in the subject.

According to further features in preferred embodiments of the invention described below, the subject is a vertebrate.

According to yet further features in preferred embodiments of the invention described below, the vertebrate is a human.

According to further features in preferred embodiments of the invention described below, the molecule which prevents activation or ligand binding of the bone cell or bone cell progenitor cannabinoid receptor is SR-141761A.

According to still further features in preferred embodiments of the invention described below, the subject suffers from a condition or disease selected from the group consisting of osteoporosis, bone fracture or deficiency, primary or secondary hyperparathyroidism, osteoarthritis, periodontal disease or defect, an osteolytic bone disease, post-plastic surgery, post-orthopedic implantation, and post-dental implantation.

According to further features in preferred embodiments of the invention described below, the method further comprising administering to the subject at least one compound capable of promoting bone formation and/or inhibiting bone resorption.

According to yet further features in preferred embodiments of the invention described below, the at least one compound is selected from the group consisting of a bone morphogenetic protein, an anti-resorptive agent, an osteogenic factor, a cartilage-derived morphogenetic protein, a parathyroid hormone, IGF1, FGF, a noggin, an osteogenic growth peptide, a growth hormone, an estrogen, a bisphosphonate, a statin and a differentiating factor.

According to still further features in preferred embodiments of the invention described below, the subject suffers from a condition or disease selected from the group consisting of Paget's disease, osteoblastic bone disease, blastic metastatic bone cancer, metastatic bone disease, Hodgkin's lymphoma, degenerative sclerosis and osteomyelitis.

According to still further features in preferred embodiments of the invention described below, the method further comprising administering to the subject at least one compound capable of inhibiting bone formation and/or promoting bone resorption.

According to still another aspect of the present invention there is provided a pharmaceutical composition for modulating bone growth and/or bone remodeling, comprising an agent capable of regulating an expression or activity of at least one cannabinoid receptor of a bone cell, a compound capable of modulating bone growth and/or bone remodeling, and a pharmaceutically acceptable carrier.

According to yet another aspect of the present invention there is provided an article-of-manufacturing, comprising a packaging material and a therapeutically effective amount of a pharmaceutical composition being identified for the treatment of a bone disease or a bone defect, the pharmaceutical composition including an agent capable of regulating activity or expression of at least one cannabinoid receptor and a pharmaceutically acceptable carrier.

According to further features in preferred embodiments of the invention described below, the at least one compound is selected from the group consisting of a bone morphogenetic protein, an anti-resorptive agent, an osteogenic factor, a cartilage-derived morphogenetic protein, a parathyroid hormone, IGF1, FGF, a noggin, an osteogenic growth peptide, a growth hormone, an estrogen, a bisphosphonate, a statin and a differentiating factor.

According to yet further features in preferred embodiments of the invention described below, the pharmaceutical composition comprising at least one compound capable of inhibiting bone formation or promoting bone resorption.

According to an additional aspect of the present invention there is provided a method of identifying a bone growth modulating agent, comprising screening a plurality of molecules to thereby uncover a molecule capable of regulating an expression or activity of at least one cannabinoid receptor, the molecule being the bone growth modulating agent.

According to further features in preferred embodiments of the invention described below, the method further comprising determining an ability of the molecule to modify bone formation rate and/or altering bone mineralization perimeter.

According to yet further features in preferred embodiments of the invention described below the screening is effected by exposing bone cells to the plurality of molecules and determining the expression of at least one cannabinoid receptor in the bone cells.

According to further features in preferred embodiments of the invention described below, the at least one cannabinoid receptor is a bone cell or bone cell progenitor cannabinoid receptor.

According to yet further features in preferred embodiments of the invention described below, expression of the cannabinoid receptor is determined by RT-PCR or real time RT-PCR.

According to yet further features in preferred embodiments of the invention described below, the bone cell progenitor is an osteogenic cell, a stromal cell or a bone resorbing cell progenitor.

According to still further features in preferred embodiments of the invention described below, the regulating is upregulating, wherein the upregulating of the expression or activity is effected by an agent, or administering to the subject at least one agent selected from the group consisting of: (a) an exogenous polynucleotide sequence designed and constructed to express at least a functional portion of the at least one cannabinoid receptor; (b) a compound which increases an expression of an endogenous DNA or mRNA encoding the at least one cannabinoid receptor; and (c) a molecule which activates the at least one cannabinoid receptor.

According to further features in preferred embodiments of the invention described below, the molecule which activates the at least one cannabinoid receptor is a cannabinoid.

According to still further features in preferred embodiments of the invention described below, the cannabinoid is selected from the group consisting of $\Delta^9$-THC, $\Delta^8$-THC, $\Delta^9$-THC-dimethylheptyl, HU-210, 5'-F-$\Delta^8$-THC, 11-OH-cannabinol, $\Delta^8$-THC-11-oic-dimethylheptyl acid, JWH-051, 11-Hydroxy THCs, desacetyl-L-nantradol, 11-OH-cannabinol-dimethylheptyl, cannabinol-dimethylheptyl-11-oic acid, HU-308, HU 243, L-759633, L-759656, L-768242, JWH-133, JWH-139, JWH-051, JWH-015, CP55940, CP47497, CP55244, R-(+)-WIN55212, ACEA, ACPA, O-1812, anandamide, 2AG, 2-arachidonoylglyceryl ether and methanandamide.

According to still further features in preferred embodiments of the invention described below, the cannabinoid is HU-308.

According to still further features in preferred embodiments of the invention described below, the cannabinoid is 2AG.

According to yet further features in preferred embodiments of the invention described below, the regulating is downregulating, wherein the downregulating of the expression or activity is effected by an agent, or administering to the subject at least one agent selected from the group consisting of: (a) a molecule which binds the at least one cannabinoid receptor; (b) an enzyme which cleaves the at least one cannabinoid receptor; (c) an siRNA molecule capable of inducing degradation of mRNA transcripts of the at least one cannabinoid receptor; (d) a DNAzyme which specifically cleaves mRNA transcripts or DNA of the at least one cannabinoid receptor; (e) an antisense polynucleotide capable of specifically hybridizing with an mRNA transcript encoding the at least one cannabinoid receptor; (f) a ribozyme which specifically cleaves mRNA transcripts encoding the at least one cannabinoid receptor; (g) a non-functional analogue of at least a binding portion of the at least one cannabinoid receptor; and (h) a molecule which prevents activation or ligand binding of the at least one cannabinoid receptor.

According to still further features in preferred embodiments of the invention described below, the regulating of the expression or activity is effected by upregulating a first cannabinoid receptor of the at least one cannabinoid receptor and downregulating a second cannabinoid receptor of the at least one cannabinoid receptor.

According to further features in preferred embodiments of the invention described below, the at least one cannabinoid receptor is selected from the group consisting of a CB1 receptor, a CB1-like receptor, a CB2 receptor, a CB2-like receptor and a non-CB1 non-CB2 receptor.

The present invention successfully addresses the shortcomings of the presently known configurations by providing methods of modulating bone growth and, remodeling, methods of treating or preventing bone diseases, methods of inducing bone growth and peak bone mass or repair by regulation of the expression or activity of cannabinoid receptors in bone cells. Specifically, the cannabinoid receptor-mediated effects, acting on both osteoblast (bone forming) and osteoclast (bone resorbing) activities, provide new methods for prevention as well as therapeutic intervention in diverse bone diseases. Also provided are pharmaceutical compositions for modulating bone growth and/or bone remodeling, articles of manufacturing and methods of identifying bone growth modulating agents based on cannabinoid receptor-mediated effects.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 1A-B illustrate qualitative micro-computed tomography ($\mu$CT) of femora of male $CB1^{-/-}$ [CB1 cannabinoid receptor knockout (deficient) mice] and of the wild type control (WT). FIGS. 1A and 1B show three dimensional $\mu$CT images indicating a marked decrease of trabecular bone-volume density in the distal femoral metaphysis of $CB1^{-/-}$ (FIG. 1A), as well as diminishing of the trabecular connectivity in the $CB1^{-/-}$ mice (FIG. 1A). The images were taken from representative femora with median trabecular bone volume density values.

FIGS. 2A-E illustrate comparative morphometric analyses of micro-computed tomography ($\mu$CT) of femora of male $CB1^{-/-}$ [CB1 cannabinoid receptor knockout (deficient) mice] and of the wild type control (WT). FIG. 2A (top left) shows a significant increase of cortical thickness in $CB1^{-/-}$ mice ($p=0.012$); FIG. 2B (top right) shows a significant decrease in medullary space volume in $CB1^{-/-}$ mice ($p=0.003$); FIG. 2C (bottom left) shows a significant decrease of trabecular bone volume in $CB1^{-/-}$ mice ($p=0.018$); FIG. 2D (bottom middle) shows a significant decrease of trabecular number decrease in $CB1^{-/-}$ mice ($p=0.0003$); and FIG. 2E (bottom right) shows a significant decrease of trabecular connectivity in $CB1^{-/-}$ mice ($p=0.0002$). The error bars indicate±standard error.

Figure 3B:
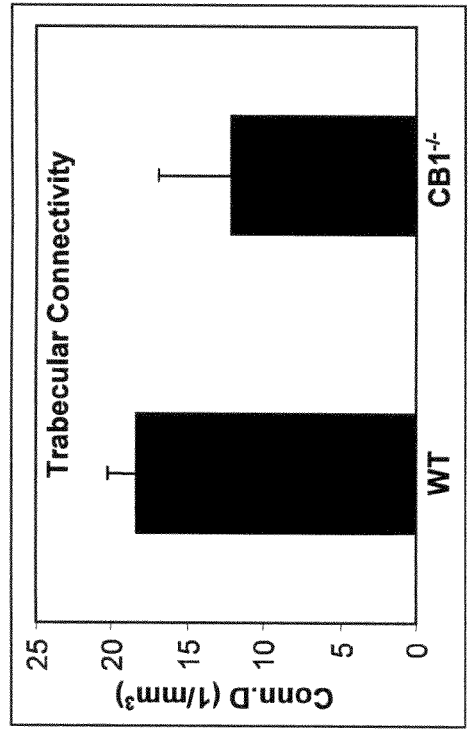
Figure 3D:
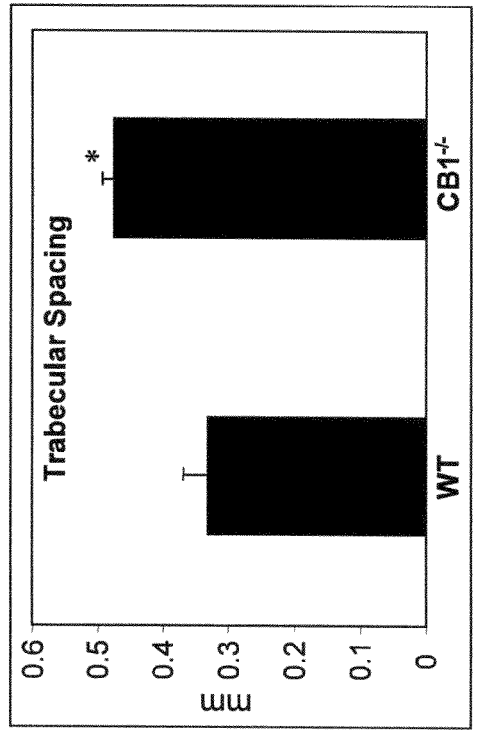
Figure 3A:
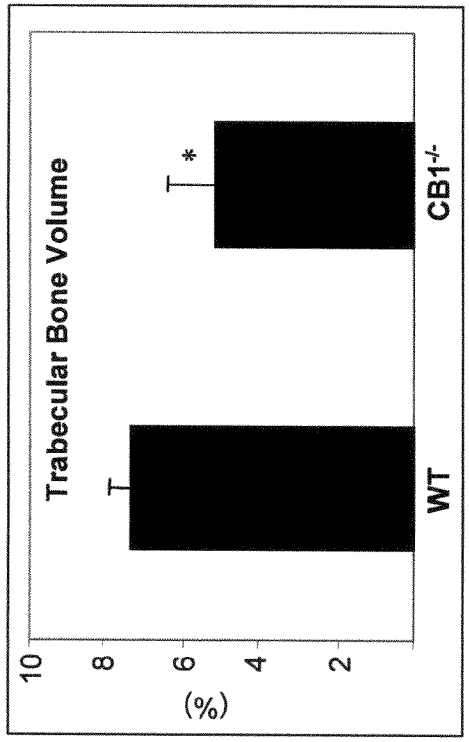
Figure 3C:
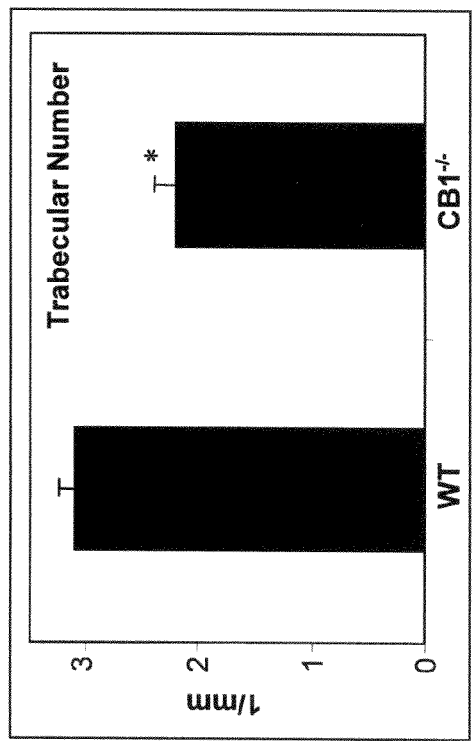

FIGS. 3A-D illustrate micro computed-tomographic ($\mu$CT) morphometric analyses of femora of female CB1 receptor-knockout (deficient) mice ($CB1^{-/-}$) in comparison with female wild type control (WT). The error bars indicate±standard error and the asterisks indicate statistical significance. FIG. 3A (top left) shows a significant decrease of trabecular bone volume in $CB1^{-/-}$ mice; FIG. 3B (top right) shows a non-significant decrease of trabecular connectivity in $CB1^{-/-}$ mice; FIG. 3C (bottom left) shows a significant decrease of trabecular number in $CB1^{-/-}$ mice; while FIG. 3D (bottom right) shows a significant increase of trabecular spacing in $CB1^{-/-}$ mice.

Figure 4B:
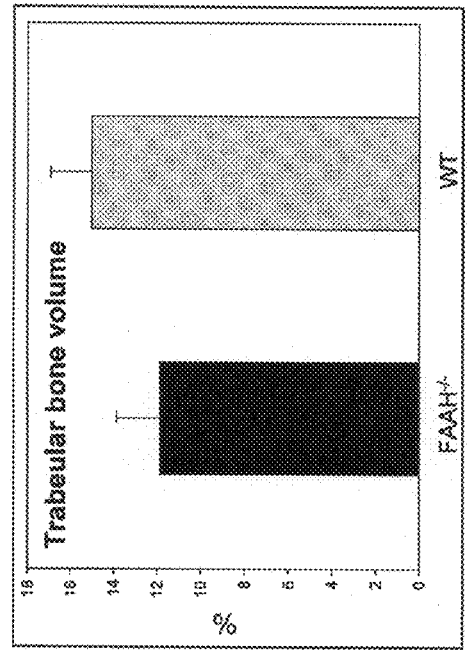
Figure 4D:
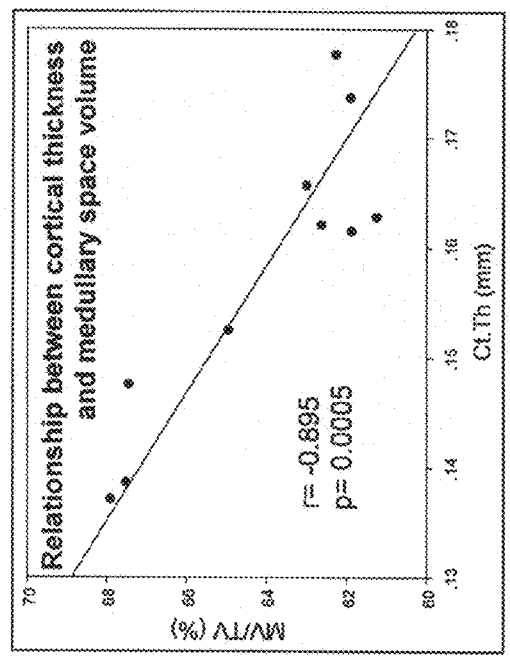
Figure 4A:
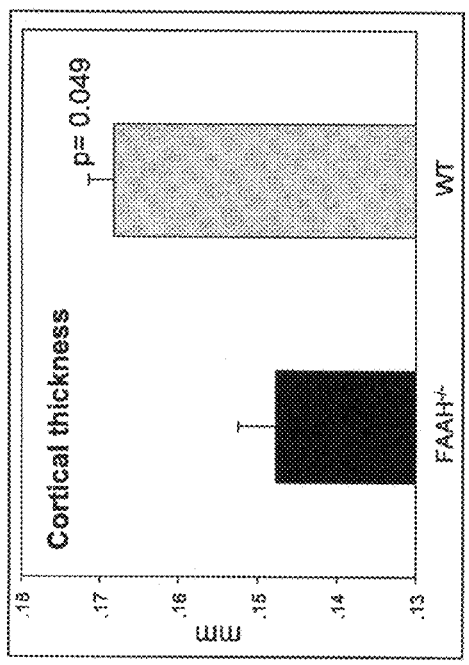
Figure 4C:
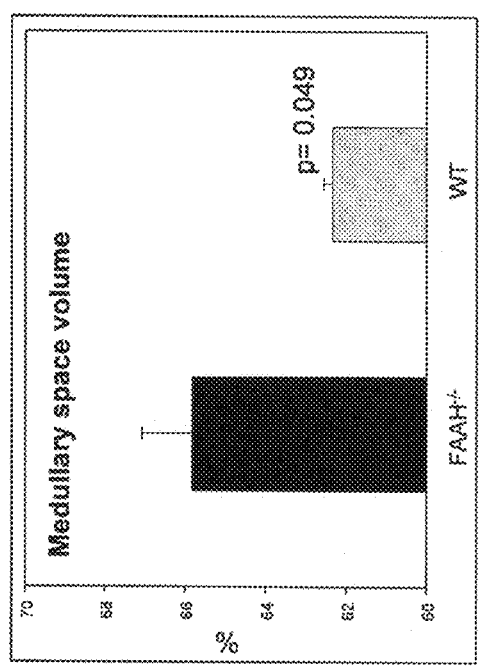

FIGS. 4A-D illustrate $\mu$CT morphometric analyses of femora of male $FAAH^{-/-}$ [fatty-acid amide hydrolase (FAAH) knockout (deficient) mice] and of the wild type control (WT). The error bars indicate±standard error. FIG. 4A (top left) shows a significant decrease the cortical thickness in $FAAH^{-/-}$ mice ($p=0.049$); FIG. 4B (top right) shows a non-significant decrease of trabecular bone volume $FAAH^{-/-}$ mice; while FIG. 4C (bottom left) show a significant increase of medullary space volume in $FAAH^{-/-}$ mice. FIG. 4D shows a linear regression analysis between the bone cortical thickness (Ct. Th.) and the medullary space volume (MV/TV), indicating a significant inverse correlation ($r=-0.985$, $p=0.005$).

Figure 5:
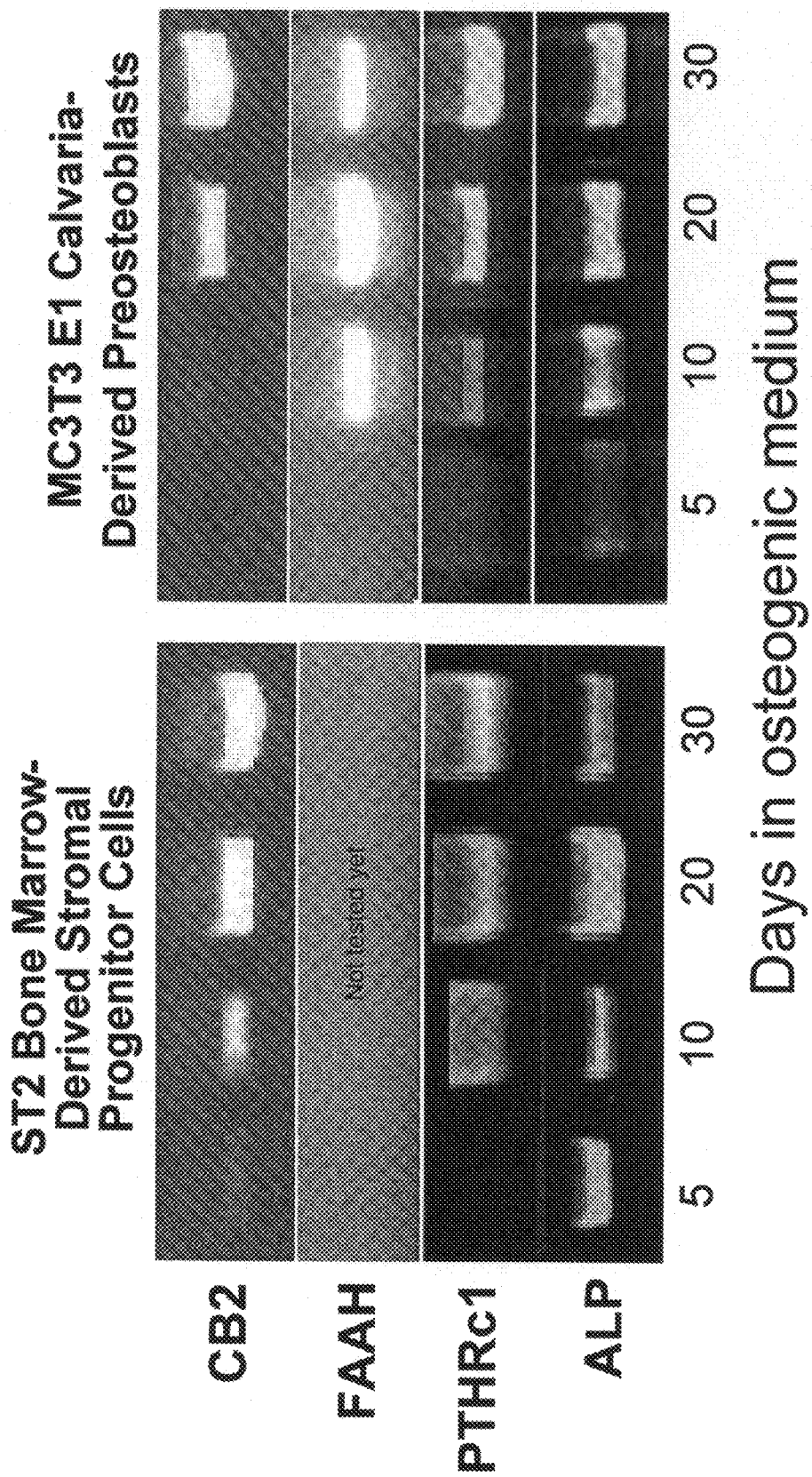

FIG. 5 illustrates RT-PCR expression analyses of CB2 cannabinoid receptor, fatty acid amide hydrolase (FAAH), parathyroid hormone receptor (PTHRc1) and tissue-nonspecific alkaline phosphatase (ALP), in differentiating osteoblast progenitor cells. Note that the RT-PCR analyses of ST2 bone-marrow derived stromal progenitor cells (left panel) reveals CB2 gene expression from as early as 5 days in osteogenic medium, while the RT-PCR analyses of MC3T3 E1 calvaria-derived osteoblast cells (right panel) indicate a much later appearance of CB2 receptor expression (10 and 20 days).

FIGS. 6A-C illustrate expression of the cannabinoid receptor CB2 and of fatty-acid amide hydrolase (FAAH) in differentiating osteoclasts. FIG. 6A (left panel) is a micrograph of femoral monocytes cultured in osteoclast differentiation medium containing M-CSF and RANKL (osteoclast differentiating factors). FIG. 6B (right panel) is a micrograph of differentiating osteoclasts stained with tartarate-resistant acid phosphatase. Differentiated osteoclasts are stained red to pink red color. FIG. 6C (bottom) is a RT-PCR analysis which illustrates a positive expression of CB2 and of FAAH in both cultured monocytes and differentiated osteoclasts.

Figure 7A:
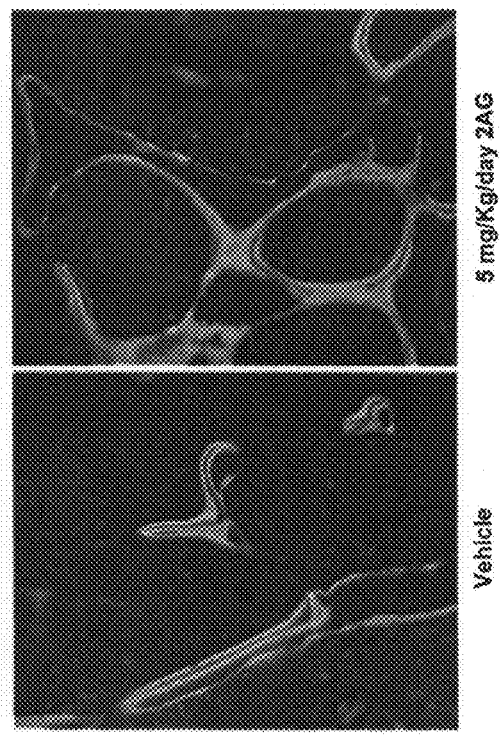
Figure 7B:
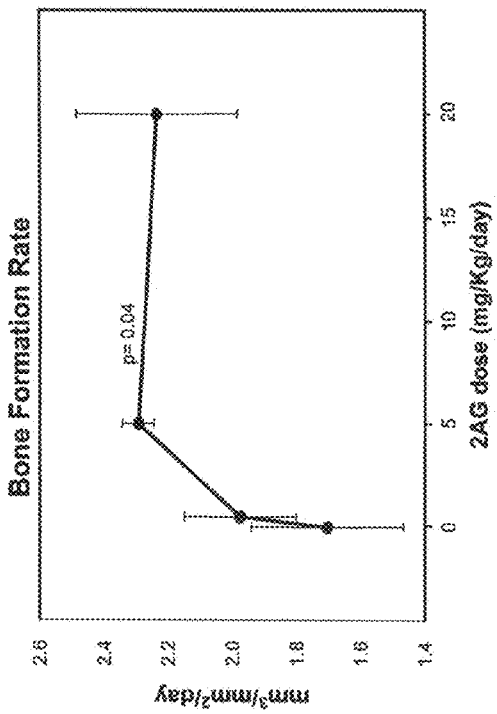
Figure 7D:
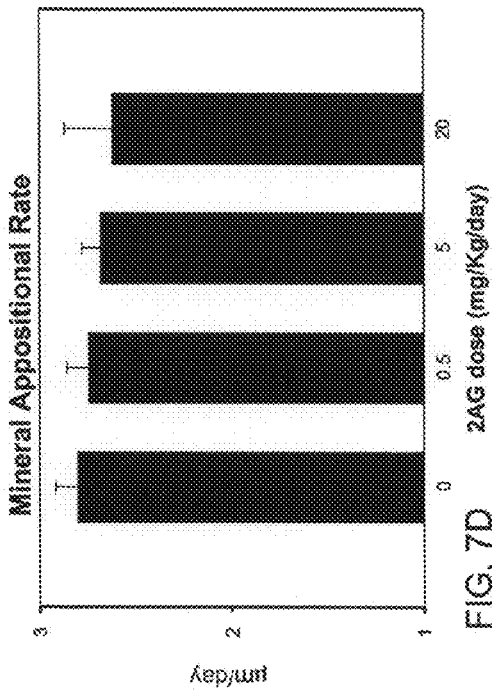
Figure 7C:
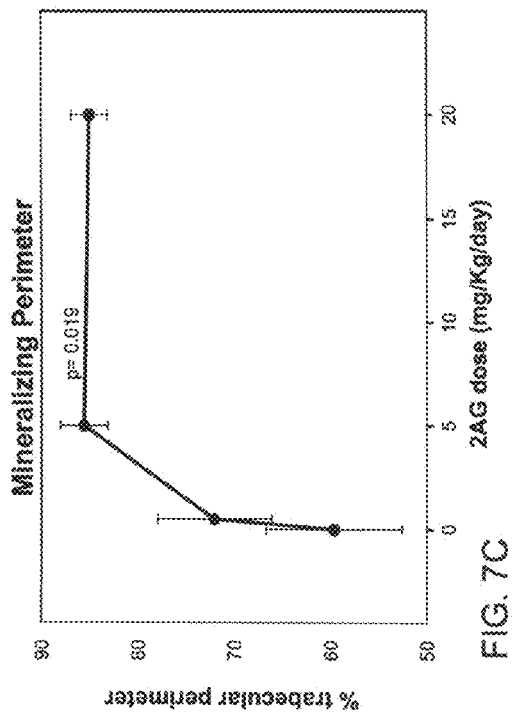

FIGS. 7A-D illustrate qualitative and histomorphometric analyses of mice treated or untreated with the endocannabinoid 2-arachidonoyl glycerol (2AG). FIG. 7A (top left) shows a significant positive dose response effect of 2AG on bone formation rate (p=0.04). FIG. 7B (top right) shows representative fluorescent histological images of 2AG treated (2AG) and untreated (vehicle) mice, revealing the incorporation of calcein staining into sites of bone formation. Note the increased density of fluorescent calcein staining, indicating the higher density of mineralization fronts, in the 2AG-treated mice (right panel). The bone tissue of a 2AG treated mouse (right image) appears substantially denser than a similar bone tissue of an untreated mouse (left image). FIG. 7C (bottom left) shows a similar significant positive dose response effect of 2AG on mineralizing perimeter (p=0.019). However, no significant effect of 2AG on mineral appositional rate was evident (FIG. 7D, bottom right).

Figure 8A:
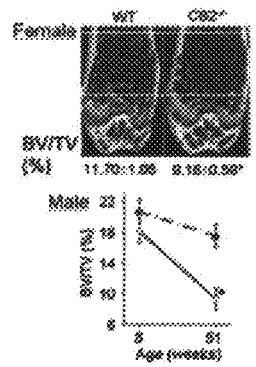
Figure 8B:
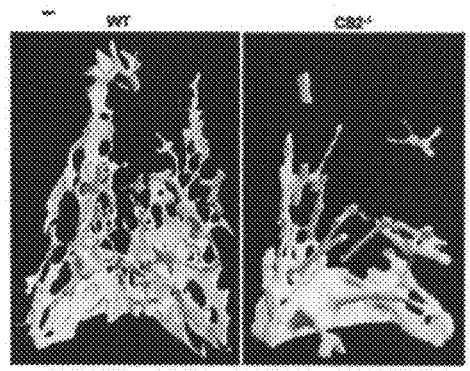
Figure 8C:
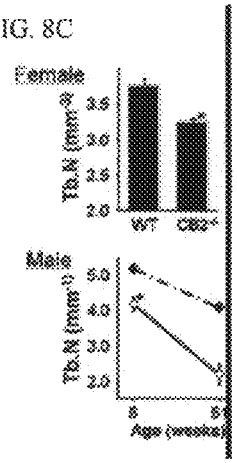
Figure 8D:
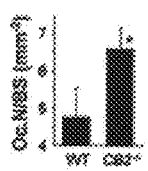
Figure 8E:
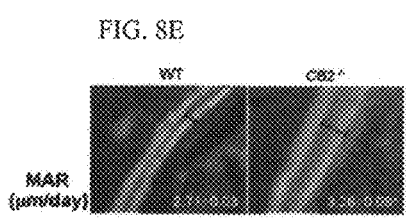
Figure 8F:
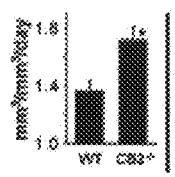

FIGS. 8A-F illustrate low trabecular bone mass/high bone turnover phenotype in $CB2^{-/-}$ mice. FIG. 8A is a µCT analysis of a distal femoral metaphysis showing trabecular bone volume density as percent trabecular network of total metaphyseal volume (BV/TV). Horizontal lines indicate proximal and distal borders of metaphyseal reference compartment. FIG. 8B shows a tri-dimensional trabecular bone structure in 51 week old male mice. FIG. 8C shows trabecular number per $mm^3$ of metaphyseal reference volume (Tb.N). Empty circles, $CB2^{-/-}$ mice; filled circles, control mice. FIGS. 8D-F illustrate histomorphometric analyses performed in distal femoral metaphysis of 8-week old female mice. FIG. 8D shows osteoclast number per trabecular $mm^2$ of trabecular surface area. Osteoclasts were identified using TRAP staining. FIG. 8E shows a trabecular mineral appositional rate (MAR). FIG. 8F shows bone formation rate (BFR). Parameters in FIGS. 8E-F were determined using vital double labelling with calcein fluorochrome. Quantitative data are mean values±SE; * indicates significant difference at $p<0.05$.

Figure 9:
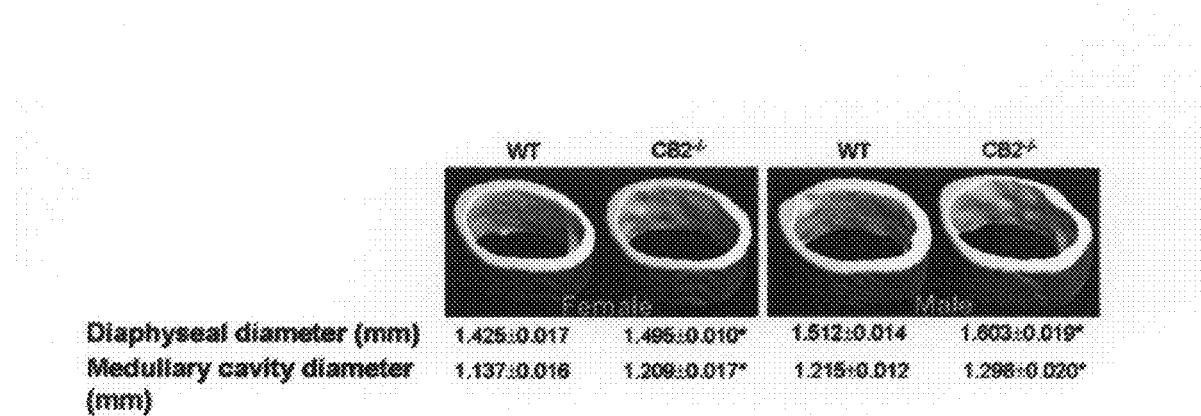

FIG. 9 is a µCT analysis illustrating cortical expansion in femoral mid-diaphysis of 8-week old $CB2^{-/-}$ mice. Quantitative data are mean values±SE; * indicates significant difference at $p<0.05$.

Figure 10A:
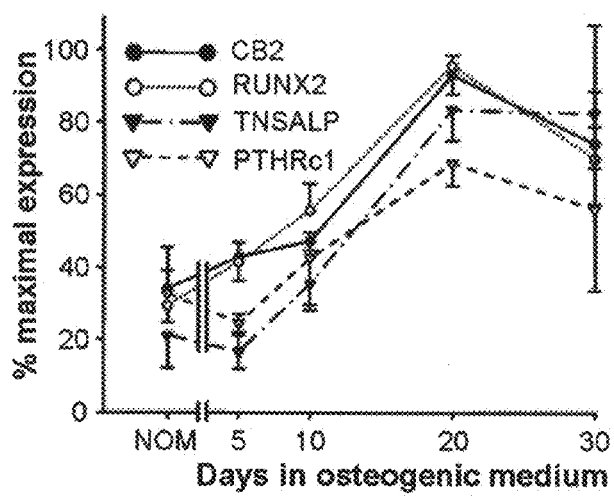
Figure 10B:
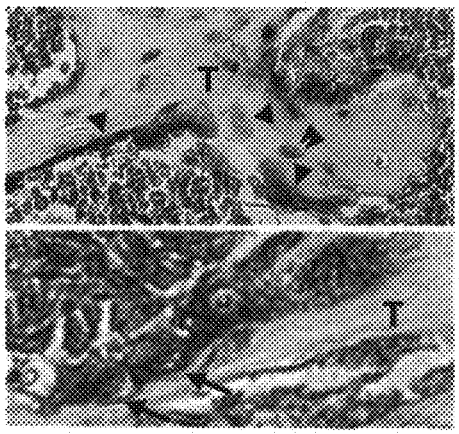
Figure 10C:
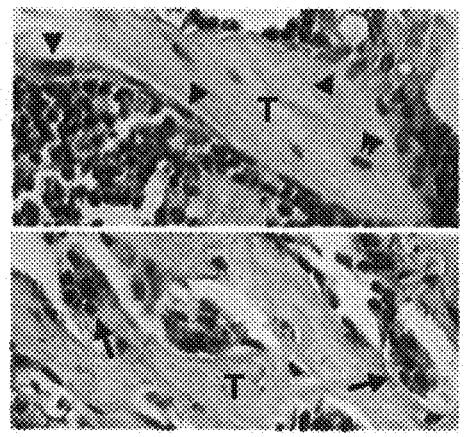

FIGS. 10A-C illustrate a CB2 expression in normal bone. FIG. 10A is a real-time RT-PCR for CB2 of osteoblast differentiation markers in stromal cells derived from murine femoral diaphyseal bone marrow undergoing osteoblastic differentiation in osteogenic medium (9). NOM, cells grown for 20 days in non-osteogenic medium; RUNX2, runt-related transcription factor 2; TNSALP, tissue non-specific alkaline phosphatase; PTHRc1 parathyroid hormone/parathyroid hormone-related protein receptor 1. FIGS. 10B-C illustrate immunohistochemical localization of CB2-positive osteoblasts (arrowheads), osteocytes (double arrowhead) and osteoclasts (arrows) in distal femoral metaphysis of WT mice (FIG. 10B), but not of $CB2^{-/-}$ mice (FIG. 10C).

Figure 11A:
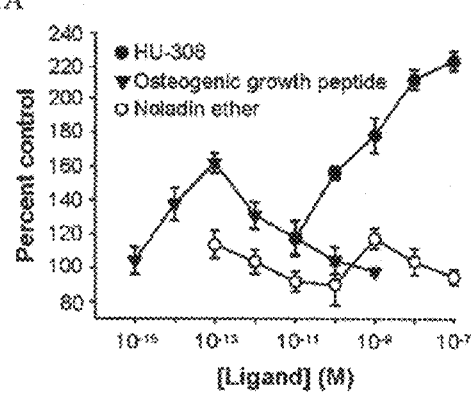
Figure 11B:
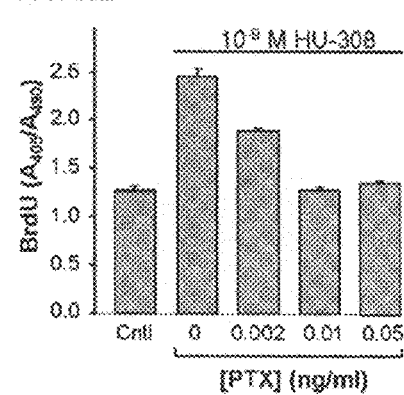

FIGS. 11A-B illustrate the mitogenic effect of the CB2 specific agonist HU-308 on partially differentiated preosteoblasts. FIG. 11A shows diaphyseal derived bone marrow stromal cells. Osteogenic growth peptide is a osteoblastic mitogen (22); noladin ether is a specific CB1 agonist (17). FIG. 11B shows pertussis toxin (PTX)-induced inhibition DNA synthesis of a MC3T3 E1 cell DNA 24 her following HU-308 treatment. Cells were grown for 10 days in osteogenic medium prior to HU-308 treatment. Data are mean values±SE obtained in triplicate culture wells per condition.

Figure 12A:
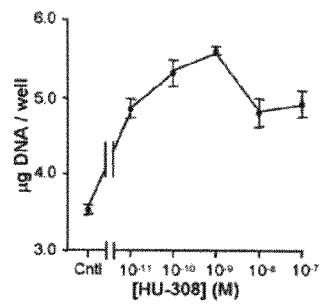
Figure 12B:
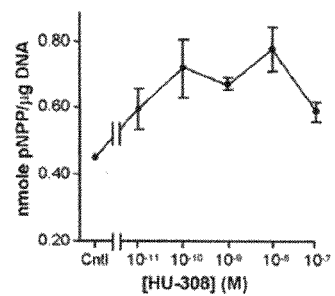
Figure 12C:
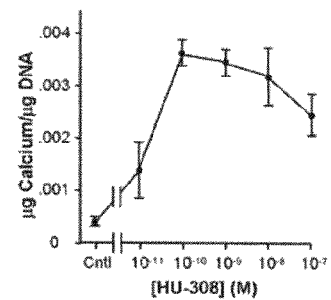

FIGS. 12A-C illustrate the stimulating effect of CB2 specific agonist HU-308 on osteoblastic activity of mature MC3T3 E1 cells. FIGS. 12A-C show cells DNA content (indicative of cell density), TNSALP activity and accumulation of external minerals (indicative of osteoblastic activity), respectively. Cells were grown for 20 days in osteogenic medium supplemented with HU-308 during the last 14 days of incubation. Data are mean values±SE obtained in triplicate culture wells per condition.

Figure 13A:
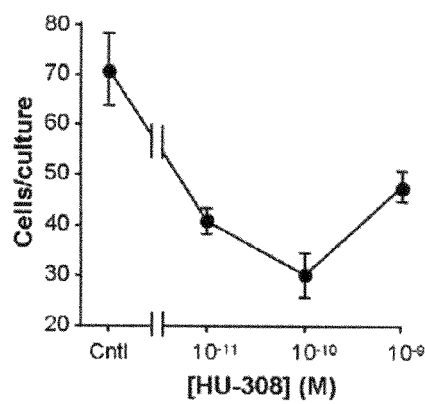
Figure 13B:
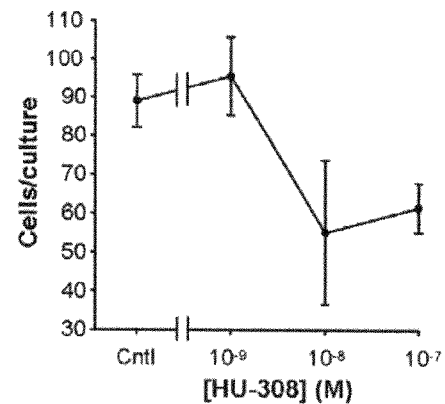

FIGS. 13A-B illustrate the inhibiting effect of CB2 specific agonist HU-308 on osteoclastogenesis. FIG. 13A shows TRAP-positive multinucleated osteoclastogenic-primary bone marrow derived monocytes which have been cultured for 5 days in medium supplemented with M-CSF and RANKL. FIG. 13B shows RAW 264.7 cells which have been cultured for 7 days in growth medium supplemented with RANKL. Data are mean values±SE obtained in triplicate culture wells per condition.

Figure 14A:
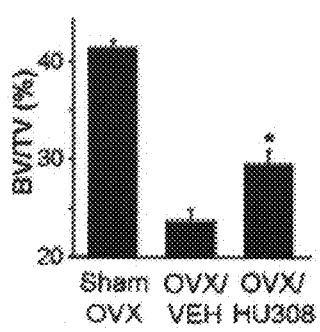
Figure 14B:
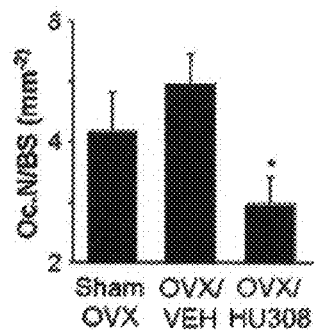
Figure 14C:
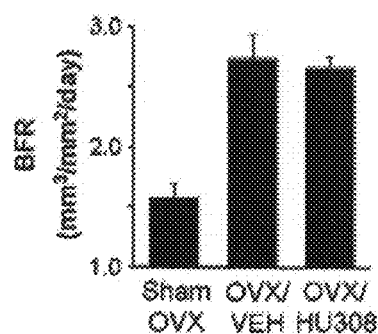
Figure 14D:
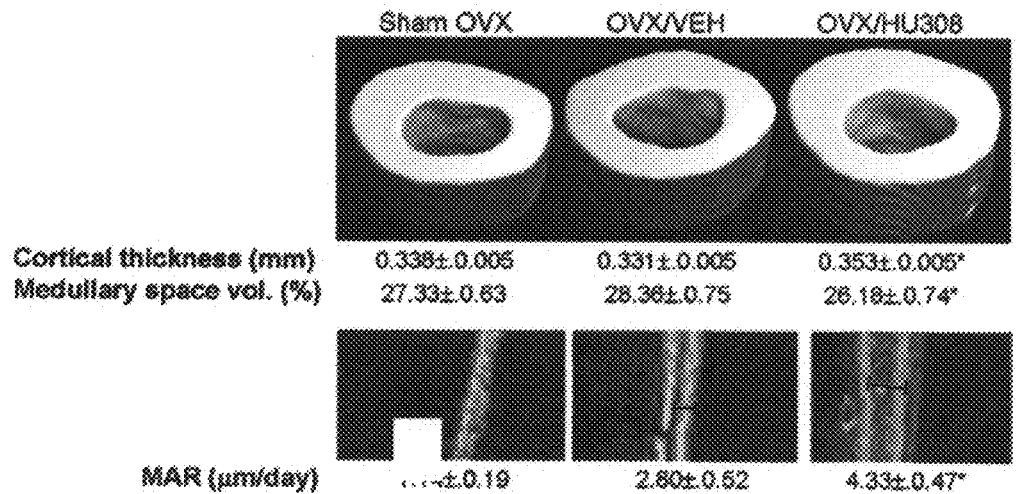

FIGS. 14A-D illustrate the attenuating effect of CB2 specific agonist HU-308 on OVX-induced femoral bone loss in sexually mature C3H mice. HU-308 was administered to mice at 10 mg/Kg/day over a 4 week period commenced at the time of ovariectomy. FIG. 14A is a µCT analysis of trabecular bone volume density. FIG. 14B is a histomorphometric analysis of osteoclast number. FIG. 14C is a histomorphometric analysis of bone formation rate. FIGS. 14A-C were analysed in the distal femoral metaphysis. FIG. 14D shows a mid-diaphyseal µCT analysis (top) and a histomorphometric analysis. Quantitative microtomograpic and histomorphometric parameters are as defined in FIGS. 8A-F. Data are mean values±SE; * indicates significant difference at $p<0.05$.

DESCRIPTION OF THE PREFERRED EMBODIMENTS

The present invention relates to methods and pharmaceutical compositions suitable for modulating bone growth and remodeling, preventing bone diseases and inducing bone growth or repair. The present invention also relates to methods of identifying bone growth modulating agents. The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Cannabinoid receptors belong to the superfamily of G-protein coupled receptors. They are classified into the predominantly neuronal CB1 receptors and the predominantly peripheral CB2 receptors. While the effects of CB1 receptors are principally associated with the central nervous system, CB2 receptors are believed to have peripheral effects related to immunomodulation and inflammation. In addition to the CB1 and CB2 receptors, recent pharmacological evidence indicates possible existence of additional types of cannabinoid receptors [e.g., Breivogel et al., Mol Pharmacol 60: 155-163 (2001); Calignano A., Eur J Pharmacol 419: 191-198 (2001); Jarai et al., Proc Natl Acad Sci USA 96: 14136-14141 (1999); and Di Marzo et al., J. Neurochem 75: 2434-2444 (2000)].

Upregulation of CB1 receptors inhibits transmitter release, while upregulation of CB2 receptors inhibits monocyte/macrophage activity and the release of inflammatory cytokines [Howlett et al., Pharmacol. Rev. 54:161-202 (2002)]. Accordingly, ligands of cannabinoids receptors have been described as therapeutic agents for treating a range of diseases or disorders which relate to this described function of these receptors.

While reducing the present invention to practice the present inventors surprisingly and unexpectedly discovered that cannabinoid receptors are expressed in bone cells and participate in regulation of bone formation, remodeling and bone growth (see Examples 1-4 of the Examples section which follows).

As used herein, the term "bone growth" is defined as including all processes resulting in a maintenance of or positive increase in amount and integrity of bone tissue. Particularly, bone growth includes bone remodeling, bone formation, mineralization, etc.

The expression of cannabinoid receptors in bone tissue, the regulatory effect of cannabinoid receptors on bone growth and remodeling and the potential benefit of manipulating expression or activity of cannabinoid receptors for treating bone diseases have not been described, nor suggested, in prior art.

Thus, according to one aspect of the present invention there is provided a method of modulating bone growth and remodeling. The method according to this aspect is effected by regulating an expression or activity of one or more cannabinoid receptors.

The cannabinoid receptor of the present invention is preferably a bone cell or bone cell progenitor receptor. As used herein, the phrase "bone cell" refers to a skeletal tissue cell, such as, bone, cartilage, tendon, ligament, marrow stroma and connective tissue cells, including bone resorbing cells such as marrow monocyte-derived osteoclasts, macrophages and scavenger cells. As used herein, the term "bone cell progenitor" refers to a cell that can become committed, or partially committed, to a bone cell differentiation pathway, including stem cells and bone resorbing cell progenitors, but does not generally express markers or function as a mature, fully differentiated cell.

Preferably, the bone cell progenitor is a stromal or osteogenic cell, or a bone resorbing cell progenitor. As used herein, the term "stromal cell" refers to a pluripotent progenitor cell which is capable of dividing many times, and whose progeny will give rise to skeletal tissues, including cartilage, bone, tendon, ligament, marrow stroma and connective tissue [see A. Caplan J. Orthop. Res. 9:641-50 (1991)]. It will be noted that the term "stromal cell" also includes mesenchymal cells. As used herein, the term "osteogenic cell" refers to an osteoblast or a progenitor osteoblast cell, which give rise to a bone tissue.

The cannabinoid receptor of the present invention, can be, for example, a CB1 or CB2 receptor, a CB1-like, or CB2-like receptor or any other type of cannabinoid receptor [Howlett et al. Pharmacol. Rev. 54:161-202 (2002)].

As used herein, the phrase "regulating an expression or activity" refers to either upregulation or downregulation of receptor expression or activity, or in select instances upregulation of one cannabinoid receptor expression or activity and downregulation of another cannabinoid receptor expression or activity.

As is further described hereinunder, up or down regulation of cannabinoid receptor expression or activity can be utilized to treat a variety of bone diseases or disorders. Such regulation can be achieved using a variety of agents and approaches well known to the ordinary skilled artisan. The section below provides several examples of such agents starting with a description of agents which can be used to upregulate activity of cannabinoid receptors.

One example of an agent capable of upregulating activity of cannabinoid receptors is a cannabinoid molecule. The term "cannabinoid" refers to any natural or synthetic agonist of a cannabinoid receptor, or an analogs or derivative thereof. Presently known cannabinoids include, for example, $\Delta^9$-tetrahydrocannabinol ($\Delta^9$-THC), $\Delta^8$-THC, $\Delta^9$-THC-dimethylheptyl, 11'-hydroxy-$\Delta^8$-THC-dimethylheptyl (HU-210), 5'-F-$\Delta^8$-THC, 11-OH-cannabinol, $\Delta^8$-THC-11-oic-dimethylheptyl acid, 1-deoxy-11-OH-$\Delta^8$-THC-dimethylheptyl (JWH-051), 11-Hydroxy THCs, desacetyl-L-nantradol, 11-OH-cannabinol-dimethylheptyl, cannabinol-dimethylheptyl-11-oic acid, HU-308, HU 243, L-759633, L-759656, L-768242, JWH-133, JWH-139, JWH-051, JWH-015, CP55940, CP47497, CP55244, R-(+)-WIN55212, ACEA, ACPA, 0-1812, arachidonyl ethanolamide (anandamide), 2-arachidonoylglycerol (2AG), 2-arachidonoylglyceryl ether, and methanandamide, and analogs or derivatives thereof.

HU-308 [(+)-(1-a-H,-(3-H,5-a-H)-4-(2,6-dimethoxy-4-(1,1-dimethylhept-yl)phenyl]-6,6 dimethylbicycloj3.1.1]hept-2-ene-2-carbinol] is having the formula I described below and can be synthesized as described by Hanus et al. (Proc. Natl. Acad. Sci. U.S.A. 96: 14228-14233, 1999) and in U.S. patent application Ser. No. 10/133,153.

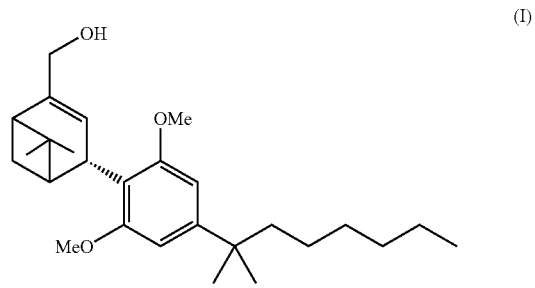

(I)

Additional cannabinoids are described in the references cited in the background section above.

Another method of upregulating receptor activity is by inhibiting metabolism of the endogenous (or exogenous) ligand, as in the SSRI (selective serotonin reuptake inhibitors) class of antidepressants or methylxanthine phosphodiesterase inhibitors upregulation of cAMP-dependent receptor activity. Inhibition of FAAH, for example (as described in the Examples section below), can effectively increase cannabinoid receptor activity.

An agent capable of upregulating expression of a cannabinoid receptor may be an exogenous polynucleotide sequence designed and constructed to express at least a functional portion of the receptor. Accordingly, the exogenous polynucleotide sequence may be a DNA or RNA sequence encoding a cannabinoid receptor molecule, capable of modulating bone growth and/or bone remodeling.

Cannabinoid receptors CB1 and CB2 have been cloned from human, rat and mouse sources [Chakrabarti et al., DNA Sequence 5: 385-388 (1995); Gérard et al., Nucleic Acids Res 18: 7142 (1990); Griffin et al., J Phannacol Exp Ther 292: 886-894 (2000); Shire et al., Biochim Biophys Acta 1307: 132-136 (1996); and Munro et al., Nature 365: 61-65 (1993)]. Thus, coding sequences information for both CB1 and CB2 is available from several databases including the GenBank database available through the U.S. National Institutes of Health-National Center for Biotechnology Information (NCBI) website.

To express exogenous cannabinoid receptors in mammalian cells, a polynucleotide sequence encoding a cannabinoid receptor (for example, CB1 receptor cDNA: GenBank Accession No. NM007726; CB2 receptor cDNA: GenBank Accession No. NM001841) is preferably ligated into a nucleic acid construct suitable for mammalian cell expression. Such a nucleic acid construct includes a promoter sequence for directing transcription of the polynucleotide sequence in the cell in a constitutive or inducible manner. A suitable promoter can be, for example, a human osteocalcin gene promoter which is capable of directing bone specific gene expression (see U.S. Pat. No. 5,948,951), or the human collagenase 1 (MMP-1) promoter (GenBank Accession No. AF023338). The nucleic acid construct of the present invention can further include additional polynucleotide sequences such as for example, sequences encoding selection markers or reporter polypeptides, sequences encoding origin of replication in bacteria, sequences that allow for translation of several proteins from a single mRNA (IRES), sequences for genomic integration of the promoter-chimeric polypeptide encoding region and/or sequences generally included in mammalian expression vector such as pcDNA3, pcDNA3.1 (+/−), pZeoSV2(+/−), pSecTag2, pDisplay, pEF/myc/cyto, pCMV/myc/cyto, pCR3.1, which are available from Invitrogen, pCI which is available from Promega, pBK-RSV and pBK-CMV which are available from Stratagene, pTRES which is available from Clontech, and their derivatives.

An agent capable of upregulating a cannabinoid receptor may also be any compound which is capable of increasing the transcription and/or translation of an endogenous DNA or mRNA encoding the cannabinoid receptor.

As is mentioned hereinabove, the method according to this aspect of the present invention also provides downgulation of expression or activity of at least one cannabinoid receptor.

One example of an agent capable of downregulating a cannabinoid receptor is an antibody or antibody fragment capable of specifically binding a cannabinoid receptor. Preferably, the antibody specifically binds at least one epitope of a cannabinoid receptor. Preferably, this epitope resides in an extracellular portion or most preferably, a ligand binding portion of the cannabinoid receptor. Examples of anti-cannabinoid receptor antibodies suitable for use in downregulation of cannabinoid receptor activity are the specific antibodies for CB1 described by Katona et al (J. Neurosci 1999; 19:4544-58).

As used herein, the term "epitope" implies any antigenic determinant on an antigen to which the paratope of an antibody binds.

Epitopic determinants usually consist of chemically active surface groupings of molecules such as amino acids or carbohydrate side chains and usually have specific three-dimensional structural characteristics, as well as specific charge characteristics.

The term "antibody" as used in this invention includes intact molecules as well as functional fragments thereof, such as Fab, F(ab')2, and Fv that are capable of binding to macrophages. These functional antibody fragments are defined as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) (Fab')2, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference). Specifically, several cannabinoid $CB_1$ and $CB_2$ receptor-specific antibodies have been successfully developed and described by Egertová et al., J Comp Neurol 422: 159-171 (2000); Tsou et al., Neuroscience 83: 393-411(1998); Daaka et al., J Pharmacol Exp Ther 276: 776-783 (1996); Sinha et al., J Neuroimmunol 82: 13-21 (1998); Waksman et al., J Pharmacol Exp Ther 288: 1357-1366; Galiègue et al., Eur J Biochem 232: 54-61(1995); and Carayon et al., Blood 92: 3605-3615 (1998).

Antibody fragments according to the present invention can be prepared by proteolytic hydrolysis of the antibody or by expression in E. coli or mammalian cells (e.g. Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. [Biochem. J. 73: 119-126 (1959)]. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al. [Proc. Nat'l Acad. Sci. USA 69:2659-62 (19720]. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by [Whitlow and Filpula, Methods 2: 97-105 (1991); Bird et al., Science 242:423-426 (1988); Pack et al., Bio/Technology 11:1271-77 (1993); and U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry [Methods, 2: 106-10 (1991)].

Humanized forms of non-human (e.g., murine) antibodies are chimeric molecules of immunoglobulins, immunoglobulin chains or fragments thereof (such as Fv, Fab, Fab', F(ab').sub.2 or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995).

Downregulating of a cannabinoid receptor may also be effected by an enzyme which cleaves the cannabinoid receptor.

Another agent capable of downregulating a cannabinoid receptor is a small interfering RNA (siRNA) molecule. RNA interference is a two step process. the first step, which is termed as the initiation step, input dsRNA is digested into 21-23 nucleotide (nt) small interfering RNAs (siRNA), probably by the action of Dicer, a member of the RNase III family of dsRNA-specific ribonucleases, which processes (cleaves) dsRNA (introduced directly or via a transgene or a virus) in an ATP-dependent manner. Successive cleavage events degrade the RNA to 19-21 bp duplexes (siRNA), each with 2-nucleotide 3' overhangs [Hutvagner and Zamore Curr. Opin. Genetics and Development 12:225-232 (2002); and Bernstein Nature 409:363-366 (2001)].

In the effector step, the siRNA duplexes bind to a nuclease complex to from the RNA-induced silencing complex (RISC). An ATP-dependent unwinding of the siRNA duplex is required for activation of the RISC. The active RISC then targets the homologous transcript by base pairing interactions and cleaves the mRNA into 12 nucleotide fragments from the 3' terminus of the siRNA [Hutvagner and Zamore Curr. Opin. Genetics and Development 12:225-232 (2002); Hammond et al. (2001) Nat. Rev. Gen. 2:110-119 (2001); and Sharp Genes. Dev. 15:485-90 (2001)]. Although the mechanism of cleavage is still to be elucidated, research indicates that each RISC contains a single siRNA and an RNase [Hutvagner and Zamore Curr. Opin. Genetics and Development 12:225-232 (2002)].

Because of the remarkable potency of RNAi, an amplification step within the RNAi pathway has been suggested. Amplification could occur by copying of the input dsRNAs which would generate more siRNAs, or by replication of the siRNAs formed. Alternatively or additionally, amplification could be effected by multiple turnover events of the RISC [Hammond et al. Nat. Rev. Gen. 2:110-119 (2001), Sharp Genes. Dev. 15:485-90 (2001); Hutvagner and Zamore Curr. Opin. Genetics and Development 12:225-232 (2002)]. For more information on RNAi see the following reviews Tuschl ChemBiochem. 2:239-245 (2001); Cullen Nat. Immunol. 3:597-599 (2002); and Brantl Biochem. Biophys. Act. 1575: 15-25 (2002).

Synthesis of RNAi molecules suitable for use with the present invention can be effected as follows. First, the cannabinoid receptor mRNA sequence is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs) are richer in regulatory protein binding sites. UTR-binding proteins and/or translation initiation complexes may interfere with binding of the siRNA endonuclease complex [Tuschl ChemBiochem. 2:239-245]. It will be appreciated though, that siRNAs directed at untranslated regions may also be effective, as demonstrated for GAPDH wherein siRNA directed at the 5' UTR mediated about 90% decrease in cellular GAPDH mRNA and completely abolished protein level (www.ambion.com/techlib/tn/91/912.html).

Second, potential target sites are compared to an appropriate genomic database (e.g., human, mouse, rat etc.) using any sequence alignment software, such as the BLAST software available from the NCBI server (www.ncbi.nlm.nih.gov/BLAST/). Putative target sites which exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene.

Another agent capable of downregulating a cannabinoid receptor is a DNAzyme molecule capable of specifically cleaving an mRNA transcript or DNA sequence of the cannabinoid receptor. DNAzymes are single-stranded polynucleotides which are capable of cleaving both single and double stranded target sequences (Breaker, R. R. and Joyce, G. Chemistry and Biology 1995; 2:655; Santoro, S. W. & Joyce, G. F. Proc. Natl, Acad. Sci. USA 1997; 943:4262) A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions (Santoro, S. W. & Joyce, G. F. Proc. Natl, Acad. Sci. USA 199; for rev of DNAzymes see Khachigian, LM [Curr Opin Mol Ther 4:119-21 (2002)].

Examples of construction and amplification of synthetic, engineered DNAzymes recognizing single and double-stranded target cleavage sites have been disclosed in U.S. Pat. No. 6,326,174 to Joyce et al. DNAzymes of similar design directed against the human Urokinase receptor were recently observed to inhibit Urokinase receptor expression, and successfully inhibit colon cancer cell metastasis in vivo (Itoh et al, 20002, Abstract 409, Ann Meeting Am Soc Gen Ther www.asgt.org). In another application, DNAzymes complementary to bcr-abl oncogenes were successful in inhibiting the oncogenes expression in leukemia cells, and lessening relapse rates in autologous bone marrow transplant in cases of CML and ALL.

Downregulation of a cannabinoid receptor can also be effected by using an antisense polynucleotide capable of specifically hybridizing with an mRNA transcript encoding the cannabinoid receptor.

Design of antisense molecules which can be used to efficiently downregulate a cannabinoid receptor must be effected while considering two aspects important to the antisense approach. The first aspect is delivery of the oligonucleotide into the cytoplasm of the appropriate cells, while the second aspect is design of an oligonucleotide which specifically binds the designated mRNA within cells in a way which inhibits translation thereof.

The prior art teaches of a number of delivery strategies which can be used to efficiently deliver oligonucleotides into a wide variety of cell types [see, for example, Luft J Mol Med 76: 75-6 (1998); Kronenwett et al. Blood 91: 852-62 (1998); Rajur et al. Bioconjug Chem 8: 935-40 (1997); Lavigne et al. Biochem Biophys Res Commun 237: 566-71 (1997) and Aoki et al. (1997) Biochem Biophys Res Commun 231: 540-5 (1997)]. Of particular interest is the method described by Erikkson (U.S. Pat. No. 6,525,030) for periosteal transformation using microinjection of DNA at the bone surface.

In addition, algorithms for identifying those sequences with the highest predicted binding affinity for their target mRNA based on a thermodynamic cycle that accounts for the energetics of structural alterations in both the target mRNA and the oligonucleotide are also available [see, for example, Walton et al. Biotechnol Bioeng 65: 1-9 (1999)].

Such algorithms have been successfully used to implement an antisense approach in cells. For example, the algorithm developed by Walton et al. enabled scientists to successfully design antisense oligonucleotides for rabbit beta-globin (RBG) and mouse tumor necrosis factor-alpha (TNF alpha) transcripts. The same research group has more recently reported that the antisense activity of rationally selected oligonucleotides against three model target mRNAs (human lactate dehydrogenase A and B and rat gp130) in cell culture as evaluated by a kinetic PCR technique proved effective in almost all cases, including tests against three different targets in two cell types with phosphodiester and phosphorothioate oligonucleotide chemistries.

In addition, several approaches for designing and predicting efficiency of specific oligonucleotides using an in vitro system were also published (Matveeva et al., Nature Biotechnology 16: 1374-1375 (1998)].

Several clinical trials have demonstrated safety, feasibility and activity of antisense oligonucleotides. For example, antisense oligonucleotides suitable for the treatment of cancer have been successfully used [Holmund et al., Curr Opin Mol Ther 1:372-85 (1999)], while treatment of hematological malignancies via antisense oligonucleotides targeting c-myb gene, p53 and Bcl-2 had entered clinical trials and had been shown to be tolerated by patients [Gerwitz Curr Opin Mol Ther 1:297-306 (1999)].

More recently, antisense-mediated suppression of human heparanase gene expression has been reported to inhibit pleural dissemination of human cancer cells in a mouse model [Uno et al., Cancer Res 61:7855-60 (2001)].

Thus, the current consensus is that recent developments in the field of antisense technology which, as described above, have led to the generation of highly accurate antisense design algorithms and a wide variety of oligonucleotide delivery systems, enable an ordinarily skilled artisan to design and implement antisense approaches suitable for downregulating expression of known sequences without having to resort to undue trial and error experimentation.

Another agent capable of downregulating a cannabinoid receptor is a ribozyme molecule capable of specifically cleaving an mRNA transcript encoding a cannabinoid receptor. Ribozymes are being increasingly used for the sequence-specific inhibition of gene expression by the cleavage of mRNAs encoding proteins of interest [Welch et al., Curr Opin Biotechnol. 9:486-96 (1998)]. The possibility of designing ribozymes to cleave any specific target RNA has rendered them valuable tools in both basic research and therapeutic applications. In the therapeutics area, ribozymes have been exploited to target viral RNAs in infectious diseases, dominant oncogenes in cancers and specific somatic mutations in genetic disorders [Welch et al., Clin Diagn Virol. 10:163-71 (1998)]. Most notably, several ribozyme gene therapy protocols for HIV patients are already in Phase 1 trials. More recently, ribozymes have been used for transgenic animal research, gene target validation and pathway elucidation. Several ribozymes are in various stages of clinical trials. ANGIOZYME was the first chemically synthesized ribozyme to be studied in human clinical trials. ANGIOZYME specifically inhibits formation of the VEGF-r (Vascular Endothelial Growth Factor receptor), a key component in the angiogenesis pathway. Ribozyme Pharmaceuticals, Inc., as well as other firms have demonstrated the importance of anti-angiogenesis therapeutics in animal models. HEPTAZYME, a ribozyme designed to selectively destroy Hepatitis C Virus (HCV) RNA, was found effective in decreasing Hepatitis C viral RNA in cell culture assays (Ribozyme Pharmaceuticals, Incorporated—WEB home page).

Another agent capable of downregulating a cannabinoid receptor can be a non-functional analogue of a binding portion of the cannabinoid receptor. Examples include truncated CB1 or CB2 sequences (lacking for example the N-terminal portion).

Yet another agent capable of downregulating a cannabinoid receptor is a molecule which can prevent activation of, or ligand binding on, the cannabinoid receptor. The molecule may be a cannabinoid antagonist or an inverse agonist, such as, for example, SR141716A, SR144528, AM251, AM281, SR144528, LY320135, AM630, WIN56098, WIN54461, O-1184 and 0-1238 [see in Howlett et al., Pharmacol. Rev. 54:161-202 (2002)].

Cannabinoid receptor activity can also be downregulated by specifically targeting the natural ligand of the cannabinoid receptor, such as anandamine, 2AG or any other endocannabinoid capable of binding a cannabinoid receptor in a bone cell.

As is mentioned hereinabove, regulation of cannabinoid receptor expression or activity can be upregulation of one or more cannabinoid receptors, downregulation of one or more cannabinoid receptors or upregulation of one receptor and downregulation of another. While the latter scenario has not yet been described in prior art in any application related to cannabinoid receptor activity, the results of Example 4 of the Examples section that follows, suggest that such a case exists with the CB1 cannabinoid-receptor antagonist SR-141761A which may also act as an agonist of another yet unknown cannabinoid receptor.

Regulation of cannabinoid receptor expression or activity may be effected ex vivo by exposing cultured bone cells to an upregulating or downregulating agent, or in vivo by administering such an agent to a subject.

Thus, according to another aspect of the present invention, there is provided a method of inducing bone growth or repair in a subject of need thereof.

The term "subject" used herein refers to human as well as other animal species, such as, for example, canine, feline, bovine, porcine, rodent, and the like.

The phrase "treating or preventing" used herein refers to a postponement of development of bone deficit symptoms and/ or a reduction in the severity of such symptoms that will or are expected to develop. These further include ameliorating existing bone or cartilage deficit symptoms, preventing additional symptoms, ameliorating or preventing the underlying metabolic causes of symptoms, preventing or reversing bone resorption and/or encouraging bone growth. Thus, the phrase denotes that a beneficial result has been conferred on a vertebrate subject with a cartilage, bone or skeletal deficit, or with the potential to develop such deficit. The phrase further refers to a postponement of development of bone overgrowth symptoms and/or a reduction in the severity of such symptoms that will or are expected to develop.

The method can be effected using two alternative approaches. In a first approach, bone cells are isolated from the subject or an allogeneic or syngeneic donor and expression or activity of one or more cannabinoid receptors of these bone cells is either downregulated or preferably upregulated (or both) as described above. Once expression or activity is either upregulated or downregulated cells displaying modified cannabinoid receptor activity are administered to the subject (preferably via local injection).

In a second approach, the agent is directly administered to the subject via one of several alternative administration modes (further described hereinbelow).

The above described approaches can be utilized to treat a variety of bone related diseases or disorders. For example, agents capable of upregulating cannabinoid receptor expression or activity can be used for treating or preventing any bone deficit-related disease or condition such as, for example, preventing bone defects and deficiencies in closed, open and non-union fractures; augmenting bone mass in young individuals at risk; prophylactic treatment in young individuals by enhancing peak bone mass in closed and open fracture reduction; promotion of bone healing in plastic surgery; stimulation of bone ingrowth into non-cemented post orthopedic and dental implants; elevation of peak bone mass in pre-menopausal women; treatment of growth deficiencies; treatment of primary or secondary hyperparathyroidism; treatment of osteolytic bone disease such as cancer; treatment of periodontal disease and defects, and other tooth repair processes; increase in bone formation during distraction osteogenesis; and treatment of other skeletal disorders, such as age-related osteoporosis, post-menopausal osteoporosis, glucocorticoid-induced osteoporosis or disuse osteoporosis and arthritis, osteoarthritis or any condition that benefits from stimulation of bone formation, on the one hand, and inhibition of bone resorption, on the other. The agents of the present invention can also be useful in repair of congenital, traumainduced or surgical resection of bone (for instance, for cancer treatment), and in cosmetic surgery. Further, the compounds of the present invention can be used for limiting or treating cartilage defects or disorders, and may be useful in wound healing or tissue repair.

Agents capable of downregulating cannabinoid receptors, such as described hereinabove, can be used for treating or preventing any bone overgrowth-related disease or condition such as, for example, certain stages of Paget's disease, an osteoblastic bone disease, a metastatic bone disease such as breast cancer and prostate cancer, a blastic metastatic bone cancer, Hodgkin's lymphoma, degenerative sclerosis and osteomyelitis.

The agents of the present invention can be in therapy per se or as part (active ingredient) of a pharmaceutical composition.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

A pharmaceutical composition which includes one or more cannabinoid receptor upregulating agents may also include one or more compounds which promote bone formation and/or inhibiting bone resorption, such as, for example, a bone morphogenic factors, bone morphogenic protein, parathyroid hormone, noggin, osteogenic growth peptide, anti-resorptive agents, osteogenic factors, cartilage-derived morphogenic proteins, growth hormones, cytokines such as fibroblast growth factor (FGF), insulin-like growth factor-I (IGF-I), transforming growth factors, estrogens, bisphosphonates, statin, calcitonin, dihydroxy vitamin $D_3$, and calcium preparations are preferred for this purpose.

Alternatively, a pharmaceutical composition which includes one or more cannabinoid receptor downregulating agents may also include one or more compounds which inhibit bone formation and/or promote bone resorption.

Further, up- or downregulating agents can be targeted to bone or other specific sites of activity using targeting molecules.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, inrtaperitoneal, intranasal, or intraocular injections.

Alternately, one may administer the pharmaceutical composition in a local rather than systemic manner, for example, via injection of the pharmaceutical composition directly into a bone tissue region of a patient.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. One route of administration which is suited for the pharmaceutical compositions of the present invention is sub-periosteal injection, as described in U.S. Pat. No. 6,525,030 to Erikkson. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as crosslinked polyvinyl pyrrolidone, agar, or alginic acid or a salt thereof such as sodium alginate. As used herein, the term "oral administration" includes administration of the pharmaceutical compound to any oral surface, including the tongue, gums, palate, or other buccal surfaces. Addition methods of oral administration include provision of the pharmaceutical composition in a mist, spray or suspension compatible with tissues of the oral surface.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients (e.g. antisense oligonucleotide) effective to prevent, alleviate or ameliorate symptoms of a disorder (e.g., mammary tumor progression) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in an animal model, such as the murine Neu model [Muller et al., Cell 54, 105-115 (1988)], to achieve a desired concentration or titer. Other such exemplary model system suitable for use with the methods of the present invention are differentiating osteoclasts (see Example 3 hereinbelow), and differentiating cultured osteogenic cells (see Example 2 hereinbelow). Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to levels of the active ingredient which are sufficient to, for example, retard tumor progression in the case of blastic metastases (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as if further detailed above.

In order to facilitate practice of the methods described hereinabove, and/or production of pharmaceutical compositions and articles of manufacture as described hereinabove, the present invention further provides a method of identifying novel bone growth and remodeling modulating agents.

The method of identifying a drug candidate includes screening a plurality of molecules for a molecule capable of regulating an expression or activity of one or more cannabinoid receptors of bone cells. Screening may be accomplished in vitro by exposing cultured bone cell progenitors, such as murine bone marrow-derived osteoprogenitor cells (ST2 cell line) or calvaria-derived osteoblastic cells (MC3T3 E1 cell line) to test molecules followed by Reverse Transcription Polymerase Chain Reaction (RT-PCR) analysis for cannabinoid receptors expression, using a standard RT-PCR procedure, such as described in Example 2 of the Examples section which follows. Selected molecules may be further evaluated for a bone-growth modulating activity in vivo by administering selected test molecules to laboratory animals followed by determining their effect on bone growth in the treated animals. For example, a test molecule may be dissolved in 1:1:18 ethanol:emulfor:saline (v/v/v) vehicle and injected intraperitoneally to a C3H (Harlan) mouse, using a protocol such as described in Example 4 of the Examples section below. The efficacy of the test molecules may be determined by comparing the bone growth rate and/or bone mineralization perimeter in the treated mice with the bone growth parameters in similar untreated mice. Molecules which induce significant stimulation, or inhibition, of a bone growth parameter become candidate for additional evaluations as bone-growth modulating agents.

Thus, the present invention provides novel methods, compositions and articles of manufacture for use in treatment or prevention of bone diseases. Since the present invention is based on natural specific mechanisms of modulating new bone growth, it can be applied to treat or to prevent a wide range of bone deficit-related as well as bone overgrowth-related diseases safely and effectively.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Example 1

Effect of CB1 Cannabinoid Receptor Expression in Bone Cells

CB1 Expression Regulates Bone Growth and Remodeling

Materials and Methods

Animals: C57BL/6J mice [Zimmer, A. et al. Proc. Natl. Acad. Sci. USA. 96: 5780-5785 (1999)] were used as wild type control (WT) and were compared with CB1 receptor knockout mice (CB1$^{-/-}$) (Ledent et al., Science 283: 401-404 (1999)] or with fatty-acid amide hydrolase knockout mice (FAAH$^{-/-}$) [Cravatt et al., PNAS USA 2001; 198:9371-76 (2001)].

Micro-computed tomographic (µCT) analysis: Whole femora were examined by a µCT system (µACT 40, Scanco Medical AG, Basserdorf, Switzerland) equipped with a 5 µm focal spot microfocus X-ray tube as a source. A two-dimensional CCD, coupled to a thin scintillator as a detector permitted parallel acquisition of stacks including 20 tomographic images. The long axis of the femur was set parallel to the plane of the X-ray beam axis. The X-ray tube was operated at 50 KVp and 160 µA. The integration time was set to 100 ms. The scans were performed at a resolution of 20 µm in all three spatial dimensions (medium resolution mode). Two-dimensional CT images were reconstructed in 1024×1024 pixel matrices from 1000 projections using a standard convolutionbackprojection procedure with a Shepp and Logan filter. Images were stored in 3-D arrays with an isotropic voxel size of 20 µm. A constrained 3-D Gaussian filter (width: σ=0.8, support: one voxel width) was used to partly suppress the noise in the volumes. The samples were binarized using a global thresholding procedure (12). The threshold was set to 22.4% and 16.0% of the maximal gray scale value for cortical bone and trabecular bone, respectively. Morphometric parameters were determined using a direct 3-D approach (13). Trabecular bone parameters were measured in a metaphyseal segment, extending proximally from the proximal tip of the primary spongiosa to the proximal border of the distal femoral quartile. Cortical bone parameters were determined in a diaphyseal segment extending 1.12 mm distally from the midpoint between the femoral ends.

Femora obtained from ten week old CB1$^{-/-}$ and WT mice were sampled from ten weeks old mice since the WT mice reach their peak trabecular bone mass at this age. The representative µCT images displayed were obtained from mice with median bone volume density or cortical thickness values, and were thus representative. Data shown are mean±standard error (SE) obtained from 8 mice replications.

Results

Comparative three-dimensional µCT images of the secondary spongiosa in male CB1 knockout (deficient) (CB1$^{-/-}$) and wild-type (WT) mice are illustrated in FIGS. 1A and B. These images show a substantial decrease of trabecular network density and a substantial increase of bone-marrow spaces in the CB1$^{-/-}$ mice.

The µCT morphometric analyses of male CB1$^{-/-}$ mice as compared with the WT are summarized in FIGS. 2A-E. These Figures corroborate the results shown in FIGS. 1A and B: the CB1$^{-/-}$ mice developed a significantly higher cortical thickness [FIG. 2A; p=0.012 (t test)]; a significantly lower medullary space volume [FIG. 2B; p=0.003 (t test)]; a significantly lower trabecular bone volume density [FIG. 2C; BV/TV=11.5±1.7% vs. 18.8±2.1% (mean±SE), p=0.018 (t-test)]; a significantly lower trabecular number [FIG. 2D; Th.N.=1.9±0.2 mm-1 vs. 3.0±0.1 mm-1 (mean±SE), p=0.0003 (t-test)]; and a significantly lower trabecular connectivity [FIG. 2E; bottom right graph; Conn.D=21.6±3.6 mm-3 vs. 48.5±3.9 mm-3 (mean±SE), p=0.0002 (t-test)] as compared to their age-matched wild type (WT) controls.

The µCT morphoinetric analyses of female CB1$^{-/-}$ as compared with the WT are illustrated in FIGS. 3A-D. These analyses show that the metaphyseal changes observed in the female CB1$^{-/-}$ were similar to those seen with male CB1$^{-/-}$, i.e., having a decreased trabecular bone volume (FIG. 3A), a decreased trabecular connectivity (FIG. 3B), decreased trabecular number (FIG. 3C), and an increased trabecular spacing (FIG. 3D).

The µCT morphometric analyses of male fatty acid amide hydrolase knockout (deficient) mice (FAAH$^{-/-}$), having impaired endocannabinoid degradation, as compared with the WT are illustrated in FIGS. 4A-D. The Figures show that the FAAH$^{-/-}$ mice developed a significantly lower cortical thickness [FIG. 4A, top left graph; p=0.049 (t-test)]; and a significantly higher medullary space volume [FIG. 4C, left bottom graph; p=0.049 (t-test)]. These effects were expectedly the opposite from what was observed with CB1$^{-/-}$ mice (see FIGS. 4B and 4C above) since the FAAH enzyme is known to degrade endocannabinoides (Cravatt et al., PNAS USA 198:9371-76 (2001)]).

These results clearly show that CB1 knockout (deficient) mice have a substantial disruption of the trabecular structural integrity with possible severe consequences to the bone load bearing capacity, as compared with wild type controls. Because the body weight and neurological sign score of the CB1$^{-/-}$ mice do not differ from those of their WT littermates, it appears that this osteopenic phenotype of the CB1 knockout (deficient) mice is not secondary to impaired food intake or physical activity.

Hence, these results clearly demonstrate that CB1 receptor expression regulates bone growth and remodeling in mice, and that cannabinoids capable of regulating CB1 expression or activity can thereby modulate the bone growth and remodeling.

Example 2

Expression of Cannabinoid Receptors in Differentiating Cultured Osteogenic Cells Materials and Methods Cell cultures: the expression of cannabinoid receptors (Cnrs) CB1 and CB2, endocannabinoid-degrading enzyme fatty-acid amide hydrolase (FAAH), osteoblast differentiation-marker alkaline phosphatase (ALP), and osteoblast differentiation-marker parathyroid hormone-receptor I (PTH-Rc1), were analyzed in murine bone marrow-derived osteoprogenitor cells (ST2 cell line) and in calvaria-derived osteoblastic cells (MC3T3 E1 cell line). Osteoblastic differentiation of these cells was induced by growing them in "osteogenic medium" which contains ascorbic acid, dexamethasone and β-glycerophosphate [Frank et al. J. Cell. Biochem. 85: 737-746 (2002)].

Reverse Transcription Polymerase Chain Reaction (RT-PCR): RNA was extracted from cultured cells after 5, 10, 20 and 30 days of incubation and was analyzed by RT-PCR. The primers and RT-PCR methodology and conditions used for analyzing the expression receptor CB1 were essentially as described by: Noe et al. [Adv. Exp Med Biol. 437:223-9 (1998)], and by Noe et al. [Adv. Exp. Med. Biol. 493:215-21 (2001]. The primers and RT-PCR methodology and conditions used for analyzing the expression receptor CB2 were essentially as described by Lee et al. [Eur. J. Pharmacol. 423:235-41 (2001). The primers and RT-PCR methodology and conditions used for analyzing the expression of osteoblast markers tissue-nonspecific alkaline phosphatase receptor (ALP) were essentially as described by Ohkubo et al. [Br J Pharmacol. 131:1667-1672(2000). The primers and RT-PCR methodology and conditions used for analyzing the expression of parathyroid hormone receptor I (PTH-Rc1; 12) were essentially as described by Kato et al. [J. Bone Min. Res. 16:1622-1633 (2001), as follows:

```
CB1,
sense:
5'-TGGTGTATGATGTCTTTGGG-3',      (SEQ ID NO: 1)

antisense:
5'-ATGCTGGCTGTGTTATTGGC-3';       (SEQ ID NO: 2)

CB2,
sense:
5'-AACGGTGGCTTGGAGTTCAAC-3';      (SEQ ID NO: 3)

antisense:
5-'TAGGTAGCGGTCAACAGCG-GTTAG;    (SEQ ID NO: 4)

FAAH,
sense:
5'-GCCTGAAAGCTCTACTGTGTGAGC-3';  (SEQ ID NO: 5)

antisense:
5'-GAAGGTCCAGACTTGGTTGTGGCT-3',  (SEQ ID NO: 6)

ALP (Accession No. J02980),
sense:
5'-GACA-CAAGCATTCCCACTAT-3'      (SEQ ID NO: 7)
(967 ± 986);

antisense:
5'-ATCAG-CAGTAACCACAGTCA-3'      (SEQ ID NO: 8)
(1316 ± 1297);

parathyroid hormone (PTH-Rc1),
sense:
5'-CAAGAAGTGGATCATCCAGGT-3';     (SEQ ID NO: 9)

antisense:
5'-GCTGCTACTCCCACTTCGTGCTTT-3'.  (SEQ ID NO: 10)
```

Results

After 5 days in culture with the osteogenic medium, both the ST2 stromal progenitor calls and the MC3T3 calvaria derived preosteoblast cells exhibited minimal or no expression of CB1 or CB2 cannabinoid receptors. This was followed by a temporal increase to a considerably high steady level of CB2 mRNA expression by day (FIG. 5). On the other hand, no expression of CB1 mRNA was evident even in the most differentiated cells (data not shown). The CB2 expression pattern was similar to the temporal expression patterns of FAAH, ALP and PTH-Rc1 (FIG. 5) which are consistent with osteoblastic differentiation.

Hence, the positive expression of cannabinoid receptor CB2, and FAAH in differentiating progenitor osteoblasts as shown, indicates that developing osteoblasts become sensitive to endocannabinoid signaling early in osteogenesis, and that this upregulation of CB2 receptor expression, and endocannabinoid receptor activity may be crucial to induction of osteoblast differentiation and bone formation.

Example 3

Expression of Cannabinoid Receptor CB2 and FAAH in Differentiating Osteoclasts

Materials and Methods

Mouse femoral monocytes were separated on a Ficoll gradient and grown in culture for 5 days in medium containing the osteoclast differentiation factors M-CFS and RANKL as described by Zou et al FASEB J 2002; 16:274-82). At the end of incubation cultures were analyzed for CB2 and FAAH expression by RT-PCR as described above, and were stained with an osteoclast marker tartarate-resistant acid phosphatase for direct observation of differentiated osteoclasts.

Results

As illustrated in FIG. 6A-C both CB2 and FAAH are expressed in differentiating osteoclasts and their monocyte precursors. Since it is known that CB2 expression in monocyte/macrophage cells, which are osteoclast progenitors, inhibits their cellular activity (Parolaro et al Life Sci 1999; 65:637-44), these results suggest that CB2 expression in osteoclasts may similarly inhibit differentiation and cellular activity of the monocyte-derived octeoclast cells. Thus endocannabinoids, and other cannabinoid receptor ligands, can activate receptors on both osteoblast and osteoclast cells, and may on one hand suppress the bone resorptive activity of osteoclasts, while on the other hand promoting bone growth and remodeling activity of osteoblasts. Such a ligand, capable of effectively stimulating bone formation as well as inhibiting bone resorption, would constitute an ideal therapeutic agent for treating bone disorders.

Example 4

Effect of Cannabinoids on Bone Formation Activity In Vivo

Materials and Methods:

The endocannabinoid 2-arachidonoyl glycerol (2AG) and the CB1 cannabinoid receptor antagonist N-(piperidin-1-yl)-5-(4-chlorophenyl)-1-(2,4-dichlorophenyl)$_4$-methyl-1H-pyrazole-3-carboxamide hydrochloride (SR-141761A; Panikashvili et al., Nature 413: 527-531 (2001)] were dissolved in 1:1:18 ethanol:emulfor:saline (v/v/v) vehicle. Different dosages of each agent were daily injected intraperitoneally to 11 week-old C3H (Harlan) mice. 2AG was administered at 0 (vehicle control), 0.5, 5, and 20 mg/Kg body weight per day for 9 days; SR-141761A was administered at 1 and 10 mg/Kg body weight per day for 9 days.

To assess the in vivo bone formation activity the mice were given 15 mg/Kg body weight calcein intrapertoneally, four days and one day (same day as the last 2AG injection) prior to sacrifice. Femoral bones were separated immediately after sacrifice and subjected, undecalcified, to histological processing. Dynamic bone histomorphometric parameters were analyzed in the distal metaphysis (secondary spongiosa) in unstained longitudinal mid-saggital sections, using the procedure described by Parfitt et al. [J. Bone Miner. Res. 2: 595-610 (1987)]. The data obtained were statistically analyzed by Mann-Whitney U-test to determine significance of differences between the treatments.

Results

The administration of the endocannabinoid 2AG to mice at up to 5 mg/Kg/day for 9 days resulted in a dose-dependent stimulation of bone-formation rate (BFR; an expression of overall osteoblastic activity), followed by a plateau (FIG. 7A). The mice which were treated with 2AG at 5 and 20 mg/Kg/day showed substantially (up to 44%) and significantly (p=0.04) higher BFRs than the vehicle control. The osteogenic effect of 2AG administration is also evident from comparison of fluorescent histological images of the bones from mice treated with 2AG (5 mg/Kg/day), compared with their vehicle-treated controls (FIG. 7C), indicated by the visibly increased uptake of fluorescently labeled calcein in the treated animal's bone tissue. Similarly, the administration of 2AG at up to 5 mg/Kg/day resulted in a dose-dependent increase of mineralizing perimeter (MP; an expression of osteoblast number), followed by a plateau (FIG. 7B). The treatment of 2AG at 5 and 20 mg/Kg/day also resulted in substantially and significantly higher MPs than the control (p=0.019). Thus, the administration of effective dosages of 2AG to mice substantially stimulated bone accrual and bone formation activity in vivo.

Administration of the CB1 cannabinoid-receptor antagonist SR-141761A to mice at up to 10 mg/Kg/day for 9 days also resulted in higher (but not statistically different) BFR (osteoblastic activity) and in higher and statistically different MP (osteoblast number), than the vehicle control (data is not shown).

These results clearly demonstrate that the administration of the cannabinoid ligands 2AG and SR-141761A to mice substantially increased the number of osteoblasts and the bone formation rate, thereby effectively increasing bone accrual and structural integrity in the treated mice.

Example 5

Modulation of Bone Mass by Administering a Specific Agonist of CB2

Materials and Methods:

Animals: Mice with a deletion of the CNR2 gene (CB2$^{-/-}$ mice) (9) were crossed for 10 generations to wild type C57BL/6J mice to generate a congenic C57BL/6J CB2$^{-/-}$ strain. The effect of CB2 signalling on OVX-induced bone loss was analysed in normal C3H mice (Harlan, Israel) due to their high femoral bone density (10), which allows for a substantial amount of bone loss to occur. Because of the low trabecular bone volume density in C57BL/6J females (FIG. 8A), the absolute amount of OVX-induced bone loss in these animals is small and a large sample is required to achieve statistical significance. In addition, the number of calcein labelled packets (see below) in OVX C57BL/6J mice is often too small for the calculation of bone formation parameters in the trabecular compartment. HU-308, synthetic CB2 specific agonist with a MW of 414 g/mol, was prepared as described by Hildebrand et al. (11) and injected intraperitoneally to OVX and control mice once daily as ethanol/emulphor/saline (1:1:18) solution. To study bone formation, newly formed bone was vitally labelled in all reported animals by the fluorochrome calcein (Sigma), injected intraperitoneally (15 mg/Kg) four days and one day prior to sacrifice. Groups of 8-10 mice, 8-11 or 51 weeks old, were used in each experiment. The experimental protocols were approved by the Institutional Animal Care and Use Committee, Faculty of Medicine, the Hebrew University of Jerusalem, Israel and by the Regierungspräsidium Köln for the University of Bonn, Germany.

Micro-computed tomographic (μCT) analysis: The μCT Analyses were performed as described in Example 1 above.

Histomorphometry and immunohistochemistry: After μCT image acquisition, the specimens were embedded undecalcified in Technovit 9100 (Heraeus Kulzer, Wehrheim, Germany). Longitudinal sections through the mid-frontal plane were left unstained for dynamic histomorphometry based on the vital calcein double labeling. To identify osteoclasts, consecutive sections were stained for tartrate-resistant acid phosphatase (TRAP) (14). Parameters were determined according to a standardized nomenclature (15). Immunohistochemistry was performed using paraffin-embedded decalcified sections (16) with a polyclonal first antibody raised against the human CB2(20-33) peptide (Cayman Ann Arbor, Mich.; Cat. No. 101550). The same peptide (Cayman Ann Arbor, Mich.; Cat. No. 301550) was used to block protein-antibody complex formation in control staining. The antibody is highly specific for the human and mouse CB2 and does not cross react with CB1.

mRNA analysis: Primary osteoblastogenic cultures of stromal cells were prepared from femoral and tibial diaphyseal bone marrow of WT C57BL/6J mice and grown in "osteogenic medium" containing ascorbic acid, β-glycerophophate and dexamethasone (Sigma) as described by Frenkel et al. (17). Real-time RT-PCR analysis was carried out using Applied Biosystems Assay-on-Demand. Data was normalized GAPDH. Assay ID: GAPDH, Mm99999915_g1; CB1, Mm00432621_s1; CB2, Mm00438286_m1; PTHRc1, Mm00441046_m1; RUNX2, Mm00501578_m1; TNSALP, Mm00475831_m1. RT-PCR analysis was carried out using the primers described by Lee et al. (19).

In vitro effect of HU-308: Differentiating primary bone marrow stromal cells and MC3T3 E1 osteoblasts were initially incubated in osteogenic medium for 10 days followed by 2 h serum starvation. Ligands were dissolved in dimethylsulfoxide (DMSO) and further diluted to their final concentration using tissue culture medium. In the primary cultures, cells were counted after 48 h incubation in αMEM supplemented with 4% BSA and ligand. BrdU incorporation was determined in MC3T3 E1 cells after 24 h incubation with HU-308 preceded by 2 h with pertussis toxin (PTX). DNA content, tissue non-specific alkaline phosphatase (TNSALP) activity and calcium were determined in MC3T3 E1 cells grown for 20 days in osteogenic medium and supplemented with HU-308 in the last 14 days. The effect of HU-308 on osteoclast differentiation was measured in the osteoclastogenic system described above, supplemented with HU-308 dissolved initially in DMSO and diluted with medium. HU-308 was also tested in a RAW 264.7 cell grown for 7 days in RANKL-supplemented medium. For osteoclast-like cell counts the cultures were fixed in ethanol and TRAP-stained.

Statistical Analyses: Differences between CB2$^{-/-}$ and WT mice were analysed by t-test. HU-308 and vehicle treated OVX and sham-OVX mice were analysed by ANOVA. When significant differences were indicated by ANOVA, group means were compared using the Tukey test for pairwise comparisons.

Results

Low bone mass phenotype and high bone turnover in CB2$^{-/-}$ mice: CB2$^{-/-}$ mice are healthy, fertile and of size and weight as their age matched wild type controls (9). The present skeletal analysis shows a LBM phenotype in both male and female CB2$^{-/-}$ mice. The trabecular bone volume density (BV/TV) and trabecular number density (Tb.N) were significantly lower in these mice already at the age of 8 weeks (FIGS. 8A and 8C top). The findings in one year old mice indicate progressive, marked trabecular bone loss: the BV/TV and Tb.N in these animals were approximately half compared to age-matched WT controls (FIGS. 8A bottom, 8B and 8C). The osteoclast number (Oc.N/BS) was almost 40% higher in the CB2-1-mice (FIG. 8D). An approximately 20% increases in mineral appositional rate (MAR) and bone formation rate (BFR) was observed (FIGS. 8E-F), indicating that the LBM in these mice is associated with high bone turnover (as observed in many osteopenic states in humans and experimental animals). Another feature reminiscent of human osteoporosis is the cortical expansion (23), consisting of increased total diaphyseal and medullary cavity diameters (FIG. 9). These observations indicate that the CB2 receptor signaling is essential for in the maintenance of normal trabecular and cortical bone structure.

Expression of cannabinoid receptors in osteoblasts: In order to explore the mechanism involved in the effect of CB2 signaling in bone, its expression was analysed in mouse bone marrow-derived stromal cells whose osteoblastic differentiation was promoted using "osteogenic medium" (17). This system demonstrated progressive expression of CB2 mRNA which paralleled the expression of the osteoblastic marker genes TNSALP (encoding tissue non-specific alkaline phosphatase) and PTHRc1 (encoding PTH receptor 1) and particularly RUNX2 (24). When the cells were grown in non-osteogenic medium the CB2 mRNA level was very low (FIG. 3A). Immunohistochemical analysis in the distal femoral metaphysis clearly demonstrated CB2 receptors in osteoblasts, osteocytes and osteoclasts in normal mice (FIG. 10B), but not in $CB2^{-/-}$ mice (FIG. 10C).

Effect of CB2 specific agonist on bone cells: In order to further investigate how CB2 activation affects bone cells, the effect of HU-308, a synthetic, highly specific small molecule CB2 agonist (11), was studied in differentiating and mature osteoblastic cells and in osteoclastogenic culture systems. HU-308 potently increased the number of diaphyseal bone marrow derived stromal cells that had been grown for 10 days in osteogenic medium (FIG. 11A) to allow for partial differentiation, thus reaching a preosteoblastic stage that included an initial increase in CB2 expression (FIG. 10A). Noladin ether, a specific CB1 agonist (27) had no significant effect (FIG. 11A). At this early differentiation stage TNSALP activity and matrix mineralization were unaffected by the CB2 ligand. Thus, the HU-308-induced increase in cell number in this system is consistent with a CB2-mediated stimulation of diaphyseal preosteoblasts, implicating preosteoblastic cell pool expansion as a mechanistic aspect of the endocannabinoid action in bone.

The homogenous osteoblastic cell line, MC3T3 E1 was used to identify the mitogenic signalling pathway triggered by activated CB2. Short-term exposure of partially differentiated MC3T3 E1 osteoblastic cells to HU-308 resulted in stimulation of DNA synthesis (FIG. 11B). Since CB2 signals via $G_{i/o}$-protein (28), it was attempted to block the CB2 mitogenic effect by pertussis toxin (PTX), a specific $G_i$-protein inhibitor. Indeed, PTX inhibited the HU-308-induced increase in BrdU uptake by the MC3T3 E1 cells (FIG. 11B), indicating CB2 mitogenic signalling via the activation of a $G_i$-protein. The effect of HU-308 on cell number (measured as DNA content) was milder in mature MC3T3 E1 osteoblasts, grown for a prolonged period of time in HU-308 osteogenic medium supplemented with this agonist (FIG. 12A). However, in this mature osteoblastic system, TNSALP activity and especially the accumulation of extracellular mineral, key osteoblastic functions, were markedly enhanced (FIGS. 12B-C).

In the diaphyseal bone marrow derived osteoclastic cell system, which was grown for 5 days in the presence of M-CSF and RANKL, HU-308 dose dependently inhibited the number of osteoclast-like cells (FIG. 13). In addition, HU-308 reduced the number of osteoclast-like cells formed in a 7-day RAW 264.7 cell culture supplemented with M-CSF, indicating that CB2 is involved in restraining osteoclast differentiation.

Attenuation of OVX-induced bone loss by HU-308: In view of the HU-308 in vitro activity, and because CB2 is only peripherally expressed, CB2 specific ligands, such as HU-308, could provide an opportunity to augment bone mass while avoiding the cannabinoid psychotropic activity. Therefore, C3H mice, known for their high bone mass (10) and thus expected high amount of OVX-induced bone loss, were used. Four weeks postoperatively, these mice showed markedly decreased bone volume density accompanied by high turnover bone loss (FIGS. 14A and 14C). In the vehicle treated mice the osteoclast number at this time point was already back to normal and was further inhibited by HU-308 (FIG. 14B), resulting in attenuation of the OVX-induced trabecular bone loss (FIG. 14A). In the trabecular compartment, HU-308 did not stimulate bone formation, which was already vastly enhanced as part of the high bone turnover triggered by OVX (FIG. 14C) (29). By contrast, HU-308 induced a marked increase in the cortical thickness, which exceeded the thickness in either OVX or sham-OVX mice (FIG. 14D top). This increase was associated with a significant reduction in the size of the medullary cavity (FIG. 14D top) and a vast stimulation of endocortical bone formation (FIG. 14D bottom), attributable to the CB2-induced increase in the diaphyseal preosteoblastic cell pool (FIG. 11A).

These results clearly demonstrate that bone growth is regulated by the cannabinoid CB2 receptor and that administering a CB2 agonist, such as HU-308, can substantially increase bone mass in treated animals.

Hence, when viewed together, the results described hereinabove show unequivocally that cannabinoid receptors expression significantly affects bone growth and remodeling. It is further demonstrated that administering agents capable of regulating the expression of cannabinoid receptor may effectively modulate bone formation both in vitro and in vivo.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

LIST OF REFERENCES CITED IN NUMERALS

Additional References are Cited in the Text

1. Rhee, M. H., Vogel, Z., Barg, J., Bayewitch, M., Levy, R., Hanus, L., Breuer, A. and Mechoulam R. 1997. Cannabinol derivatives: binding to cannabinoid receptors and inhibition of adenylylcyclase. *J. Med. Chem.* 40: 3228-3233.
2. Felder, C. C., Joyce, K. E., Briley, E. M., Mansouri, J., Mackie, K., Blond, O., Lai, Y., Ma, A. L. and Mitchell, R. L. 1995. Comparison of the pharmacology and signal transduction of the human cannabinoid CB1 and CB2 receptors. *Mol. Pharmacol.* 48: 443-450.
3. Herkenham, M., Lynn, A. B., Little, M. D., Johnson, M. R., Melvin, L. S., de Costa, B. R. and Rice, K. C. 1990. Cannabinoid receptor localization in brain. *Proc. Natl. Acad. Sci. U.S.A.* 87:1932-1936.
4. Zimmer, A., Zimmer, A. M., Hohmann, A. G., Herkenham, M. and Bonner, T. I. 1999. Increased mortality, hypoactivity, and hypoalgesia in cannabinoid CB1 receptor knockout mice. *Proc. Natl. Acad. Sci. U.S.A.* 96: 5780-5785.
5. Munro, S., Thomas, K. L. and Abu-Shaar, M. 1993. Molecular characterization of a peripheral receptor for cannabinoids. *Nature* 365:61-65.
6. Ducy, P., Amling, M., Takeda, S., Priemel, M., Schilling, A. F., Beil, F. T., Shen, J., Vinson, C., Rueger, J. M. and Karsenty, G. 2000. Leptin inhibits bone formation through a hypothalamic relay: a central control of bone mass. *Cell* 100: 197-207.
7. Baldock, P. A., Sainsbury, A., Couzens, M., Enriquez, R. F., Thomas, G. P., Gardiner, E. M. and Herzog, H. 2002. Hypothalamic Y2 receptors regulate bone formation. *J. Clin. Invest.* 109: 915-921.
8. Di Marzo, V., Goparaju, S. K., Wang, L., Liu, J., Batkai, S., Jarai, Z., Fezza, F., Miura, G. I., Palmiter, R. D., Sugiura, T. and Kunos, G. 2001. Leptin-regulated endocannabinoids are involved in maintaining food intake. *Nature* 410: 822-825.
9. Buckley, N. E., McCoy, K. L., Mezey, E., Bonner, T., Zimmer, A., Felder, C. C., Glass, M. and Zimmer, A. 2000. Immunomodulation by cannabinoids is absent in mice deficient for the cannabinoid CB(2) receptor. *Eur. J. Pharmacol.* 396: 141-149.
10. Beamer, W. G., Donahue, L. R., Rosen, C. J. and Baylink, D. J. 1996. Genetic variability in adult bone density among inbred strains of mice. *Bone.* 18:397-403.
11. Hanus, L., Breuer, A., Tchilibon, S., Shiloah, S., Goldenberg, D., Horowitz, M., Pertwee, R. G., Ross, R. A., Mechoulam, R. and Fride, E. 1999. HU-308: a specific agonist for CB(2), a peripheral cannabinoid receptor. *Proc. Natl. Acad. Sci. U.S.A.* 96: 14228-14233.
12. Müller, R. and Rüegsegger, P. 1997. Micro-tomographic imaging for the nondestructive evaluation of trabecular bone architecture. *Stud. Health Technol. Inform.* 40: 61-79.
13. Hildebrand, T., Laib, A., Müller, R., Dequeker, J. and Rüegsegger, P. 1999. Direct three-dimensional morphometric analysis of human cancellous bone: microstructural data from spine, femur, iliac crest, and calcaneus. *J. Bone Miner. Res.* 14: 1167-1174.
14. Erlebacher, A. and Derynck, R. 1996. Increased expression of TGF-beta 2 in osteoblasts results in an osteoporosis-like phenotype. *J. Cell Biol.* 132: 195-210.
15. Parfitt, A. M., Drezner, M. K., Glorieux, F. H., Kanis, J. A., Malluche, H., Meunier, P. J., Ott, S. M. and Recker, R. R. 1987. Bone histomorphometry: standardization of nomenclature, symbols, and units. Report of the ASBMR Histomorphometry Nomenclature Committee. *J. Bone Miner. Res.* 2: 595-610.
16. Ausubel, F. M. 1995. Current Protocols in Molecular Biology. Wiley Interscience. New York.
17. Frenkel, B., Capparelli, C., Van Auken, M., Baran, D., Bryan, J., Stein J. L., Stein, G. S. and Lian, J. B. 1997. Activity of the osteocalcin promoter in skeletal sites of transgenic mice and during osteoblast differentiation in bone marrow-derived stromal cell cultures: effects of age and sex. *Endocrinology* 138: 2109-2116.
18. Zou, W., Schwartz, H., Endres, S., Hartmann, G. and Bar-Shavit, Z. 2002. CpG oligonucleotides: novel regulators of osteoclast differentiation. *FASEB J* 16: 274-282.
19. Lee, S. F., Newton, C., Widen, R., Friedman, H. and Klein, T. W. 2001. Downregulation of cannabinoid receptor 2 (CB2) messenger RNA expression during in vitro stimulation of murine splenocytes with lipopolysaccharide. *Adv. Exp. Med. Biol.* 493: 223-228.
20. Wienker, T. F. and T. M. Strom. http://ihg.gsfde/cgi-bin/hwlhwal.pl
21. Sasieni, P. D. 1997. From Genotypes to Genes: Doubling the Sample Size. *Biometrics* 53: 1253-1261.
22. Elston, R. C. and Forthofer, R. 1977. Testing for Hardy-Weinberg equilibrium in small samples. *Biometrics* 33: 536-542.
23. Ammann, P. and Rizzoli, R. 2003. Bone strength and its determinants. *Osteoporos. Int.* 14 Suppl 3: S13-S18.
24. Lian, J. B., Javed, A., Zaidi, S. K., Lengner, C., Montecino, M., van Wijnen, A. J., Stein, J. L., Stein, G. S. 2004. Regulatory controls for osteoblast growth and differentiation: role of Runx/Cbfa/AML factors. *Crit. Rev. Eukaryot. Gene Expr.* 14: 1-41.
25. Ross, R. A., Brockie, H. C. and Pertwee, R. G. 2000. Inhibition of nitric oxide production in RAW264.7 macrophages by cannabinoids and palmitoylethanolamide. *Eur. J. Pharmacol.* 401: 121-130.
26. Chang, Y. H., Lee, S. T. and Lin WW. 2001. Effects of cannabinoids on LPS-stimulated inflammatory mediator release from macrophages: involvement of eicosanoids. *J. Cell. Biochem.* 81: 715-723.
27. Hanus, L., Abu-Lafi, S., Fride, E., Breuer, A., Vogel, Z., Shalev, D. E., Kustanovich, I. and Mechoulam, R. 2001. 2-arachidonyl glyceryl ether, an endogenous agonist of the cannabinoid CB1 receptor. *Proc. Natl. Acad. Sci. U.S. A.* 98: 3662-3665.
28. Rhee, M. H., Bayewitch, M., Avidor-Reiss, T., Levy, R. and Vogel, Z. 1998 Cannabinoid receptor activation differentially regulates the various adenylyl cyclase isozymes. *J. Neurochem.* 71: 1525-1534.
29. Wronski, T. J., Cintron, M. and Dann, L. M. 1988. Temporal relationship between bone loss and increased bone turnover in ovariectomized rats. *Calcif Tissue Int.* 43: 179-183.
30. Devoto, M., Shimoya, K., Caminis, J., Ott, S., Tenenhouse, A., Whyte, M. P., Sereda, L., Hall, S., Considine, E., Williams, C. J., Tromp, G., Kuivaniemi, H., Ala-Kokko, L., Prockop, D. J. and Spotila, L. D. 1998. First-stage autosomal genome screen in extended pedigrees suggests genes predisposing to low bone mineral density on chromosomes 1p, 2p and 4q. *Europ. J Hum. Genet.* 6: 151-157.
31. Devoto, M., Specchia, C., Li, H.-H., Caminis, J., Tenenhouse, A., Rodriguez, H. and Spotila, L. D. 2001. Variance component linkage analysis indicates a QTL for femoral neck bone mineral density on chromosome 1p36. *Hum. Molec. Genet.* 10: 2447-2452.

32. Valk, P., Verbakel, S., Vankan, Y., Hol, S., Mancham, S., Ploemacher, R., Mayen, A., Lowenberg, B. and Delwel, R. 1997. Anandamide, a natural ligand for the peripheral cannabinoid receptor is a novel synergistic growth factor for hematopoietic cells. *Blood* 90: 1448-1457.
33. Boyle, W. J., Simonet, W. S. and Lacey, D. L. 2003. Osteoclast differentiation and activation. *Nature* 423: 337-342.
34. Ashton, B. A., Eaglesom, C. C., Bab, I. and Owen, M. E. 1984. Distribution of fibroblastic colony forming cells in rabbit bone marrow and assay of their osteogenic potential by an in vivo diffusion chamber method. *Calcif. Tissue Int.* 36: 83-86.
35. Gonsiorek, W., Lunn, C., Fan, X., Narula, S., Lundell, D. and Hipkin, R. W. 2000. Endocannabinoid 2-arachidonyl glycerol is a full agonist through human type 2 cannabinoid receptor: antagonism by anandamide. *Mol Pharmacol.* 57: 1045-1050.
36. Gabarin, N., Gavish, H., Muhlrad, A., Chen, Y.-C., Namdar-Attar, M., Nissenson, R. A., Chorev, M., Bab, I.: Mitogenic $G_i$ Protein-MAP Kinase Signaling Cascade in MC3T3 E1 Osteogenic Cells: Activation by C-Terminal Pentapeptide of Osteogenic Growth Peptide [OGP(10-14)] and Attenuation of Activation by cAMP. *J. Cell. Biochem.*, 81:594-603, 2001.
37. Carrier E J, Kearn C S, Barkmeier A J, Breese N M, Yang W, Nithipatikom K, Pfister S L, Campbell W B, Hillard C J. Cultured rat microglial cells synthesize the endocannabinoid 2-arachidonylglycerol, which increases proliferation via a CB2 receptor-dependent mechanism. Mol Pharmacol. 2004 April; 65(4):999-1007.
38. Liu J, Batkai S, Pacher P, Harvey-White J, Wagner J A, Cravatt B F, Gao B, Kunos G.
39. Lipopolysaccharide induces anandamide synthesis in macrophages via CD14/MAPK/phosphoinositide 3-kinase/NF-kappaB independently of platelet-activating factor. J. Biol. Chem. 2003 Nov. 7; 278(45):45034-9.
40. Calvi, L. M., Sims, N. A., Hunzelman, J. L., Knight, M. C., Giovannetti, A., Saxton, J. M., Kronenberg, H. M., Baron, R. and Schipani, E. 2001. Activated parathyroid hormone/parathyroid hormone-related protein receptor in osteoblastic cells differentially affects cortical and trabecular bone. *J. Clin. Invest.* 107: 277-286.
41. Wiren, K. M., Zhang, X. W., Toombs, A. R., Kasparcova, V., Gentile, M. A., Harada, S. and Jepsen, K. J. 2004. Targeted overexpression of androgen receptor in osteoblasts: unexpected complex bone phenotype in growing animals. *Endocrinology.* 145: 3507-3522.
42. Liu, Y. Z., Liu, Y. J., Recker, R. R. and Deng, H. W. 2003. Molecular studies of identification of genes for osteoporosis: the 2002 update. *J. Endocrinol.* 177: 147-196.
43. Xie, X. Q., Chen, J. Z. and Billings, E. M. 2003. 3D structural model of the G-protein-coupled cannabinoid CB2 receptor. *Proteins* 53: 307-319.

What is claimed is:

1. A method of stimulating bone formation and inhibiting bone resorption in a subject having a bone disease or condition, comprising:

administering to the subject an effective amount of a compound that stimulates bone formation and inhibits bone resorption, wherein said compound is an agonist of a cannabinoid receptor and wherein said subject having a bone disease or condition is a subject having a disease or condition selected from the group consisting of periodontal disease or defect, osteolytic bone disease other than osteoporosis, post-plastic surgery, post-orthopedic implantation, post-dental implantation, age-related osteoporosis, osteoporosis associated with post-menopausal hormone status, primary and secondary hyperparathyroidism, disuse osteoporosis, diabetes-related osteoporosis, osteoporosis associated with depression, osteoporosis associated with hypogonadism and glucocorticoid-related osteoporosis.

2. A method in accordance with claim 1, wherein said agonist of a cannabinoid receptor is an agonist of the CB2 cannabinoid receptor.

3. A method in accordance with claim 1, wherein said agonist of a cannabinoid receptor is selected from the group consisting of $\Delta^9$-tetrahydrocannabinol ($\Delta^9$-THC), $\Delta^8$-THC, $\Delta^9$-THC-dimethylheptyl, 11-hydroxy-$\Delta^8$-THC-dimethylheptyl (HU-210), 5'-F-$\Delta^8$-THC, 11-OH-cannabinol, $\Delta^8$-THC-11-oic-dimethylheptyl acid, 1-deoxy-11-OH-$\Delta^8$-THC-dimethylheptyl (JWH-051), 11-hydroxy THCs, desacetyl-L-nantradol, 11-OH-cannabinol-dimethylheptyl, cannabinol-dimethylheptyl-11-oic acid, HU-308, HU 243, L-759633, L-759656, L-768242, JWH-133, JWH-139, JWH-051, JWH-015, CP55940, CP47497, CP55244, R-(+)-WIN55212, ACEA, ACPA, O-1812, arachidonyl ethanolamide (anandamide), 2-arachidonoylglycerol (2AG), 2-arachidonoylglyceryl ether, and methanandamide.

4. A method of stimulating bone formation and inhibiting bone resorption in a subject having a bone disease or condition, comprising:

administering to the subject an effective amount of a compound that stimulates bone formation and inhibits bone resorption, wherein said compound is an agonist of a cannabinoid receptor, which agonist is selected from the group consisting of $\Delta^9$-tetrahydrocannabinol ($\Delta^9$-THC), $\Delta^8$-THC, $\Delta^9$-THC-dimethylheptyl, 11-hydroxy-$\Delta^6$-THC-dimethylheptyl (HU-210), 5'-F-$\Delta^8$-THC, 11-cannabinol, $\Delta^8$-THC-11-oic-dimethylheptyl acid, 1-deoxy-11-OH-$\Delta^8$-THC-dimethylheptyl (JWH-051), 11-hydroxy THCs, desacetyl-L-nantradol, 11-OH-cannabinol-dimethylheptyl, cannabinol-dimethylheptyl-11-oic acid, HU-308, HU 243, L-759633, L-759656, L-768242, JWH-133, JWH-139, JWH-051, JWH-015, CP55940, CP47497, CP55244, R-(+)-WIN55212, ACEA, ACPA, O-1812, arachidonyl ethanolamide (anandamide), 2-arachidonayiglycerol (2AG), 2-arachidonayiglyceryl ether, and methanandamide.

5. A method in accordance with claim 4, wherein the subject having a bone disease or condition is a subject having a disease or condition selected from the group consisting of osteoporosis, bone fracture or deficiency, primary or secondary hyperparathyroidism, osteoarthritis, periodontal disease or defect, an osteolytic bone disease, post-plastic surgery, post-orthopedic implantation, and post-dental implantation.

6. The method of claim 1, wherein said cannabinoid is HU308.

7. The method of claim 1, wherein said bone disease or condition is selected from the group consisting of periodontal disease or defect, osteolytic bone disease other than osteoporosis, post-plastic surgery, post-orthopedic implantation, and post-dental implantation.

8. The method of claim 4, wherein said cannabinoid is HU308.

9. The method of claim 4, wherein said cannabinoid is devoid of psychotropic activity.

* * * * *

```
SEQUENCE LISTING

<160> NUMBER OF SEQ ID NOS: 10

<210> SEQ ID NO 1
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 1
tggtgtatga tgtctttggg                                                  20

<210> SEQ ID NO 2
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 2
atgctggctg tgttattggc                                                  20

<210> SEQ ID NO 3
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 3
aacggtggct tggagttcaa c                                                21

<210> SEQ ID NO 4
<211> LENGTH: 24
<212> TYPE: DNA
<213> ORGANISM: Artificial sequence
```

```
<220> FEATURE:
<223> OTHER INFORMATION: Single strand DNA oligonucleotide

<400> SEQUENCE: 4
taggtagcgg tcaacagcgg ttag                                       24

<210> SEQ ID NO 5
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 5
gcctgaaagc tctactgtgt gagc                                       24

<210> SEQ ID NO 6
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 6
gaaggtccag acttggttgt ggct                                       24

<210> SEQ ID NO 7
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 7
gacacaagca ttcccactat                                            20

<210> SEQ ID NO 8
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 8
atcagcagta accacagtca                                            20

<210> SEQ ID NO 9
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 9
caagaagtgg atcatccagg t                                          21

<210> SEQ ID NO 10
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 10
gctgctactc ccacttcgtg cttt                                       24
```